United States Patent [19]

Kluge et al.

[11] 4,046,801

[45] Sept. 6, 1977

[54] 13-CIS PROSTAGLANDIN DERIVATIVES

[75] Inventors: Arthur F. Kluge, Palo Alto; Karl G. Untch, Los Altos; John H. Fried, Palo Alto, all of Calif.

[73] Assignee: Syntex (U.S.A.) Inc., Palo Alto, Calif.

[21] Appl. No.: 530,778

[22] Filed: Dec. 9, 1974

Related U.S. Application Data

[62] Division of Ser. No. 272,880, July 18, 1972, Pat. No. 3,867,377.

[51] Int. Cl.$^2$ .......................................... C07C 177/00
[52] U.S. Cl. ................................. 560/121; 260/408; 260/410.9 R; 260/413; 260/514 D; 542/426
[58] Field of Search ............... 260/468 D, 514 D, 94, 260/410.9 R, 413, 408, 240 R

[56] References Cited

U.S. PATENT DOCUMENTS 3,873,607   3/1975   Bernady et al. ..................... 260/514

Primary Examiner—Robert Gerstl
Attorney, Agent, or Firm—Gerard A. Blaufarb; William B. Walker

[57] ABSTRACT

13-Cis prostaglandin derivatives; cis-octenol ether copper$^{(I)}$ lithium reagents and methods of making such reagents and using the reagents to prepare the 13-cis prostaglandin derivatives. The 13-cis prostaglandin derivatives exhibit prostaglandin-like pharmacological properties and are further useful as intermediates for the corresponding prostaglandin isomers having the normal 13-trans configuration.

7 Claims, No Drawings

13-CIS PROSTAGLANDIN DERIVATIVES

This is a division of application Ser. No. 272,880, filed July 18, 1972, now U.S. Pat. No. 3,867,377.

BACKGROUND OF THE INVENTION

1. The Invention

This invention relates to methods of preparing prostaglandins and prostaglandin derivatives. In a further aspect, this invention relates to 13-cis prostaglandin derivatives and methods of making such derivatives. In a still further aspect, this invention relates to cis-octenol ether copper[(I)] lithium reagents and methods of preparing such reagents. In another further aspect, this invention relates to racemic octenol ether copper[(I)] lithium reagents and also optically active (R)- or (S)-octenol ether copper[(I)] lithium reagents. In still another aspect, this invention relates to methods of preparing cis prostaglandin derivatives, using such octenol ether copper[(I)] lithium reagents. This invention also relates to methods of preparing prostaglandins by the rearrangement of 13-cis prostaglandins to the corresponding 13-trans isomers.

2. The Prior Art

Prostaglandins are a group of chemically related 20-carbon chain hydroxy fatty acids having the basic skeleton of prostanoic acids:

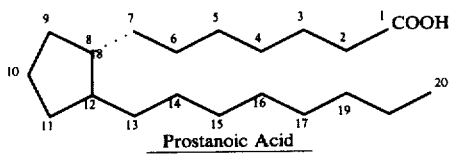

Prostanoic Acid

The prostaglandins having a hydroxy group at the C-11 position and a keto group at the C-9 position are known as the PGE series, those having a hydroxyl group in place of the keto group are known as the PGF series and are further designated by an $\alpha$ or $\beta$ suffix to indicate the configuration of the hydroxyl group at said position. The natural compounds are the 6$\beta$-hydroxy substituted compounds. They may contain different degrees of unsaturation in the molecule, particularly at C-5, C-13 and C-17, the unsaturation is also indicated by suffix. Thus, for example, $PGE_1$ refers to a prostanoic acid having a trans olefin bond at the 13-position. For a review on prostaglandins and the definition of primary prostaglandins, see, for example, S. Bergstrom, Recent Progress in Hormone Research 22, pp. 153-175 (1966) and Science 157, page 382 (1967) by the same author.

Prostaglandins are widely distributed in mammalian tissues and have been isolated from natural sources in very small amounts. In addition a number of the natural occurring prostaglandins have been prepared by chemical synthesis; note, for example, J. Am. Chem. Soc. 91, 5675 (1969), J. Am. Chem. Soc. 92, 2586 (1970) and J. Am. Chem. Soc. 93, 1489-1493 (1971) and references cited therein, W. P. Schneider et al, J. Am. Chem. Soc. 90, 5895 (1968), U. Axen et al, Chem. Commun., 303 (1969), and W. P. Schneider, Chem. Commun. 304 (1969).

Because of the remarkable range of biological and pharmacological properties exhibited by this family of compounds, a great deal of interest has focused upon such compounds and accordingly we have discovered novel 13-cis prostaglandin derivatives and felicitous high yield processes and reagents for preparing such 13-cis prostaglandin derivatives and prostaglandins.

SUMMARY OF THE INVENTION

In summary the 13-cis prostaglandin compounds of the invention can be represented by the following generic formula:

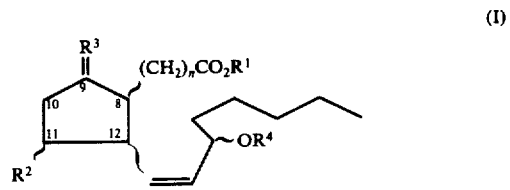

(I)

wherein n is a whole integer of from two through eight; $R^1$ is hydrogen, alkyl having from one through ten carbon atoms, chloroethyl, dichloroethyl, or trichloroethyl; $R^2$ is hydrogen, hydroxy or acid labile ether having from three through 10 carbon atoms; $R^3$ is oxo or the group

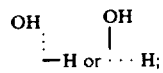

$\sim OR^4$ is hydroxy or acid labile ether and wherein the wavy line at C-15 indicates either the $\alpha$ or $\beta$ configuration or isomeric mixtures thereof and wherein the wavy lines at the C-8, C-11 and C-12 indicate that the respective configurations at C-8 and C-12 and C-11 and C-12 are both trans.

In summary the cis-octenol ether copper[(I)] lithium reagent, of the invention, comprises a complexed (dl)- or optically active (R)- or (S)-cis-1-octen-3-ol 3-ether copper[(I)] lithium in a suitable inert organic solvent mixture.

In summary the process, of the invention, for preparing the octenol ether copper[(I)] lithium reagent comprises (1) preparing a first solution by the admixture of a suitable alkyl lithium with a (dl)-, (R)- or (S)-1-iodo-cis-1-octen-3-ol 3-ether in a suitable inert organic solvent under controlled conditions; (2) preparing a copper[(I)] salt solution in a suitable inert organic solvent; (3) admixing a complexing agent with either the first solution or with the copper salt solution depending on the particular complexing agent and provided that a complexing agent is not already inherently present in the copper salt solution; and (4) admixing the first solution with the copper salt solution under controlled conditions.

In summary, the process of our invention for preparing 13-cis prostaglandin derivatives comprises treating a 2-(carboalkoxy-alkyl)-1-oxo-cyclopent-2-ene, or 4-hydroxy ethers thereof, with the complexed octenol ether copper[(I)] lithium reagnet in an inert organic solvent mixture, under reactive conditions, thereby obtaining the corresponding 13-cis-11-desoxy-prostaglandin 15-ether derivatives or the corresponding 11-ethers thereof.

In summary, the process of the invention for preparing prostaglandins comprises preparation of the corresponding 13-cis prostaglandins, followed by rearrangement of the 13-cis olefin bond to a 13-trans olefin bond.

The invention will be further described herein below.

FURTHER DESCRIPTION OF THE INVENTION AND PREFERRED EMBODIMENTS

The 13-cis prostaglandin compounds of the invention can be represented in terms of normal and retro isomer configurations by the following formulas:

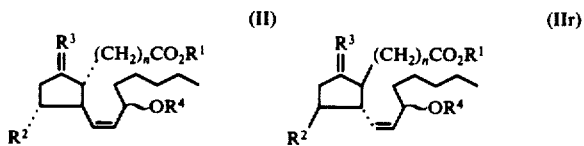

wherein $n$ is a whole integer of from two through eight; $R^1$ is hydrogen, alkyl having from one through ten carbon atoms, chloroethyl, dichloroethyl, or trichloroethyl; $R^2$ is hydrogen, hydroxy or acid labile ether having from three through 10 carbon atoms; $R^3$ is oxo or the group

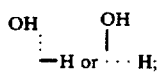

and $\sim OR^4$ is hydroxy or acid labile ether having from three through ten carbon atoms wherein the wavy bond line indicates either the $\alpha$ or $\beta$ configuration or isomer mixtures of the $\alpha$ and $\beta$ configurations.

The above formulas represent individual isomers and racemic and diastereomeric mixtures and both the respective individual isomers and racemic and diastereomeric mixtures thereof are encompassed within the invention.

Also encompassed within the invention are pharmaceutically acceptable salts of the above compounds wherein $R^1$ is hydrogen.

The preferred $R^1$ substituents are hydrogen and methyl. The preferred $R^2$ substituents are hydrogen and hydroxy. The preferred $OR^4$ substituent is hydroxy. Also, preferably $n$ is 6. The particularly preferred compounds can be represented in terms of their preferred isomer and racemic pairs by the following formulas, wherein the horizontally oriented pairs represent mirror images:

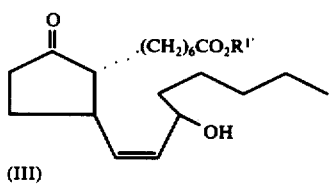
(III)

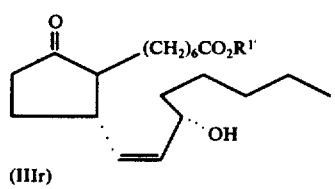
(IIIr)

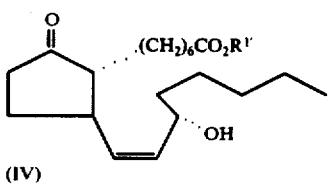
(IV)

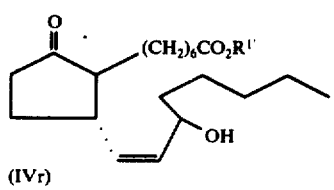
(IVr)

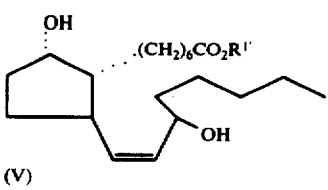
(V)

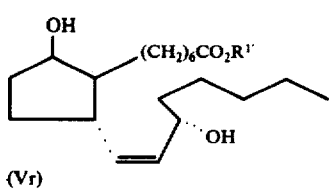
(Vr)

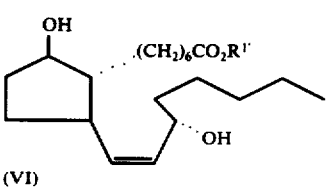
(VI)

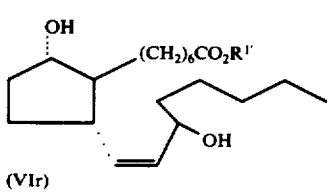
(VIr)

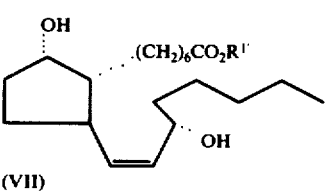
(VII)

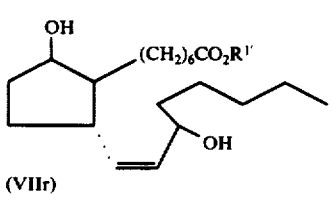
(VIIr)

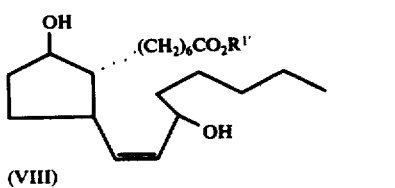
(VIII)

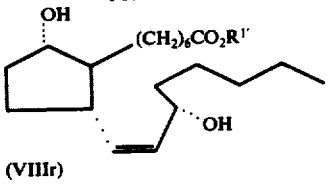
(VIIIr)

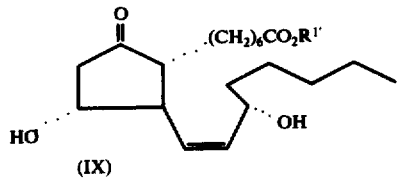
(IX)

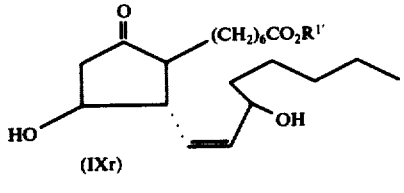
(IXr)

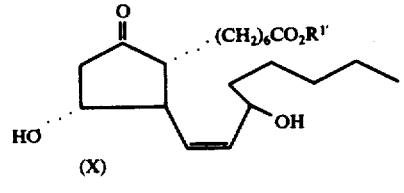
(X)

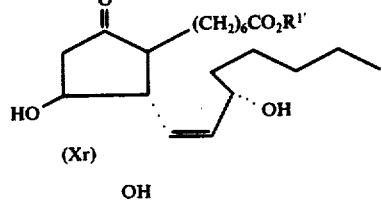
(Xr)

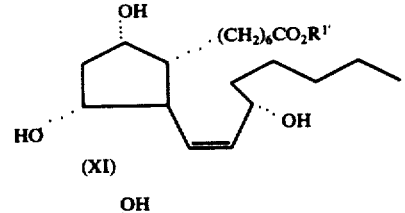
(XI)

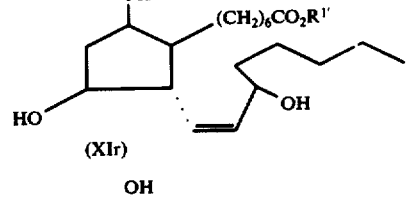
(XIr)

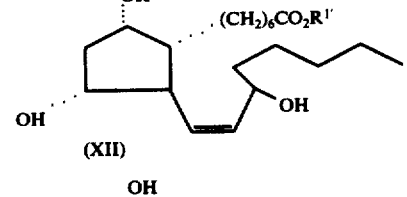
(XII)

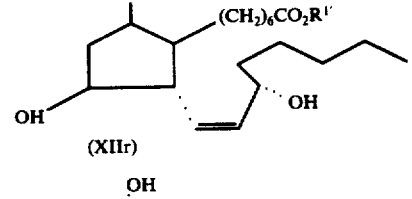
(XIIr)

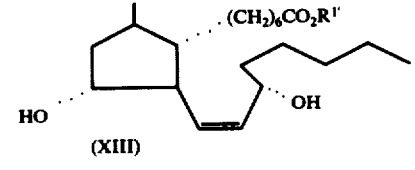
(XIII)

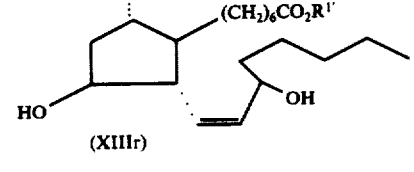
(XIIIr)

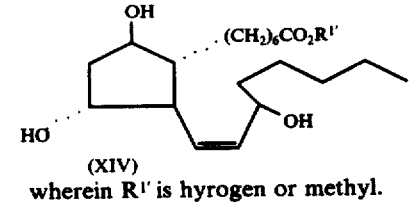
(XIV)

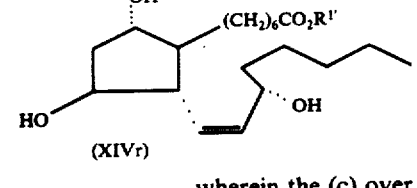
(XIVr)

wherein $R^{1'}$ is hyrogen or methyl.

Illustrations of typical 13-cis prostaglandins, of the invention, can be had herein below by reference to the Examples.

The octenol ether copper$^{(I)}$ lithium reagent of the invention is a mixture consisting essentially of (dl) and-/or optically active (R) isomers and/or optically active (S) isomers of compounds having the formulas:

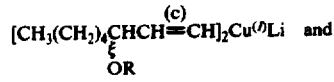

and

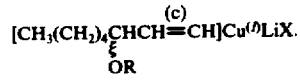

wherein the (c) over the double bond indicates the cis configuration; X is a halide; OR is an acid labile ether and the wavy line indicates either a (dl) mixture with respect to this asymmetric center or the optically active (R) or (S) isomer;

complexed by an electron-rich neutral complexing reagent, which coordinates with transition metals, in a suitable inert solvent mixture.

Typically, and preferably, the compounds of the above formulas are either a racemic (dl) mixture or the pure (R) or (S) optically active isomer. The optically active (R) and (S) isomers are especially preferred as they yield a selective β or α configuration at C-15 with respect to the corresponding asymmetric center in the 13-cis prostaglandin product. Also where it is desired to use the octenol ether copper$^{(I)}$ lithium reagent to produce a prostaglandin ether derivative having an easily cleavable 15-ether group, the preferred OR group is 2'-methoxyprop-2'-oxy.

Suitable halides are fluoride, chloride, bromide, and iodide. The preferred halide is iodide. Suitable inert solvent mixtures include, for example, mixtures of alkane and ether solvents. Suitable alkane solvents include, for example, pentane, hexane, heptane, and the like. Suitable ether solvents include diethyl ether, methyl ethyl ether and the like. The preferred solvent mixture is a mixture of hexane and diethyl ether. Typically, a solvent concentration is in the range of about from 0.5 to 50 wt. %, preferably 2 to 10%, based on the octenol ether component is used. However, the particular solvent concentration used is largely a matter of convenience and concentrations both above and below this range can also be used.

Suitable complexing reagents include, for example; (1) alkylalkylenediamines having the formula $R_1'R_2'N-(CH_2)_n-NR_3'R_4'$ wherein $n$ is the whole integer 2 or 3, and $R_1'$, $R_2'$, $R_3'$ and $R_4'$ are independently selected from the group of alkyls having from one through four carbon atoms. Thus, suitable alkylalkylenediamines include, for example, N,N,N',N'-tetramethylmethylenediamine and N,N,N',N'-tetramethylpropylenediamines. etc.; (2) naphthalene bridge diamines having the formula:

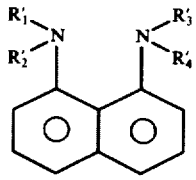

wherein $R_1'$, $R_2'$, $R_3'$ and $R_4'$ are as defined herein above;
(3) alkylpiperazines having the formula:

wherein $R_1'$ and $R_2'$ are as defined herein above;
(4) polycyclic diazoheterocyclics such as, for example, sparteine; and the like; (5) trialkyl ($C_1$ through $C_4$) phosphites such as, for example, trimethylphosphite, triethylphosphite; tri(n-propyl)phosphite; triisopropylphosphite; tri(n-butyl)phosphite; triisobutylphosphite; and the like; trialkyl ($C_1$ through $C_4$) phosphines such as, for example, trimethylphosphine; tri(n-propyl)phosphine; triisopropylphosphine; triisobutylphosphine; tri(n-butyl)phosphine; triethylphosphine; and the like. Combination complexing reagent-copper salts such as, for example, bis-(trimethylphosphite) copper$^{(l)}$ iodide and the like.

The preferred complexing reagents are tetraalkylalkylenediamines, as defined above, trialkylphosphites selected from the group consisting of trimethylphosphite, triethylphosphite, tri(n-propyl)phosphite, triisopropylphosphite, tri(n-butyl)phosphite, and triisobutylphosphite; trialkylphosphines selected from the group consisting of trimethylphosphine, triethylphosphine, tri(n-propyl)phosphine, triisopropylphosphine, tri(n-butyl)phosphine and triisobutylphosphine; and the combination complexing reagent and copper$^{(l)}$ halide slat, bis(trimethylphosphite) copper$^{(l)}$ iodide. The especially preferred complexing reagents are N,N,N', N'-tetramethylethylenediamine; trimethylphosphite; tri(n-butyl) phosphine and bis(trimethylphosphite) copper$^{(l)}$ iodide.

Definitions

As used herein above and below, the following terms have the following meanings unless expressly stated to the contrary. The term alkyl includes both straight chain and branched chain alkyl groups having from one though 10 carbon atoms. The term lower alkyl refers to both straight chain and branched chain alkyl groups having from one through six carbon atoms. The ter lower alkoxy refers to the group —OR" wherein R" is lower alkyl. The term cycloalkyl refers to cycloalkyl groups having from five through seven carbon atoms such as, for example, cyclopentyl, cyclohexyl and the like.

The term acid labile ether refers to those acid labile ether groups which can be cleaved by mild acid hydrolysis, and preferably having from three through 10 carbon atoms. Typical acid labile ether groups include, for example, 1'-methoxyprop-2'-oxy; 1'-methoxyethoxy; 1'-ethoxyethoxy; phenoxymethoxy; 2'-methoxyprop 2'-oxy; tetrahydropyranyl-2'-oxy; tetrahydrofuran-2'-oxy; 2'-butoxyprop-2'-oxy; 1'-pent-1"-oxycyclohexyl-1'-oxy; and the like.

The terms acid and base labile acyloxy groups and acid and base hydrolyzable acyl groups refer to acid labile esters and acyl groups and base labile ester and acyl groups conventionally employed in the art, preferably those derived from carboxylic acids of one to 12 carbon atoms. Typical hydrolyzable acyl groups thus include, acetyl, propionyl, butyryl, t-butyryl, valeryl, isovaleryl, hexanoyl, heptanoyl, octanoyl, nonanoyl, undecanoyl, lauroyl, benzoyl, p-methoxybenzoyl, p-nitrobenzoyl, phenylacetyl, phenylpropionyl, o-, m-, p-methylbennzoyl, β-cyclopentylpropionyl, dihydrocinnanyl, and the like.

The term complexing reagent refers to electron-rich neutral substances, commonly referred to as ligands, which are capable of coordination with transition metals. Typical ligands include, for example, tertiary amines, phosphines, phosphites, sulfides, cyanides, isonitriles and the like.

The term halide refers to fluoride, chloride, bromide, and iodide.

The prostaglandin and prostaglandin derivatives have been described herein above and below, as prostanoic acid derivatives. the term prostanoic acid refers to the structural configuration inicated herein above in the Prior Art discussion.

The term (dl) refers generally to racemic mixtures and where used as a prefix to a particular isomer structure, or word formula, it designates a racemic mixture of the indicated isomer and its mirror image. Thus, for example, the formula (dl)-9-oxo-11α-hydroxy-15α-hydroxy-prost-cis-13-enoic acid refers to an equal mixture of the indicated structure and its mirror image:

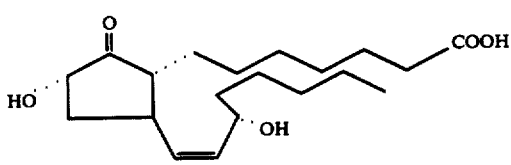
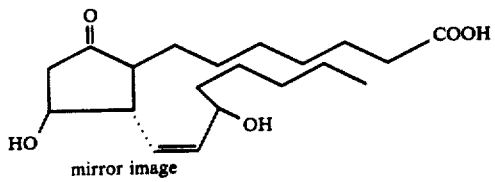

10

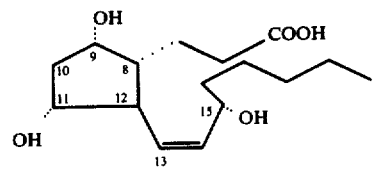

wherein tthe dotted bond line indicates the α configuration and the solid bond line indicates the β configuration.

The term retro designates one isomer of an actual or hypothetical isomer pair wherein the side chain, attached to the C-8 and C-12 positions of prostanoic acid, have the opposite configuration to the preceding reference isomer (which has the C-8, C-12 configuration of prostanoic acid), and with respect to retro compounds, the term epi indicates a substituent configuration, the same as the preceding reference isomer at that position. The cis or trans double bond orientation is the same in both the reference isomer and its retro isomer. Thus, for example, 9α, 11α,15α-trihydroxy-prost-cis-13-enoic acid has the structural configuration:

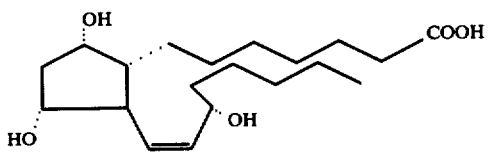

and accordingly retro-9β,11β,15-epi-trihydroxy-prost-cis-13-enoic acid refers to the structural configuration:

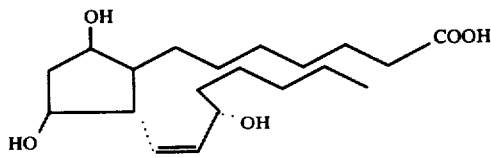

The above structure could also be named as retro-9β,11β,15α-trihydroxy-prost-cis-13-enoic acid.

Also the designation 13-cis-PGE$_1$ or PGF$_1$ refers to an isomer having the same configuration as the prostaglandin isomer designated by convention as PGE$_1$ or PGF$_1$ but having the cis configuration with respect to the 13-olefin double bond instead of trans. Similarly, the terms retro-13-cis-PGE$_1$ and retro-13-cis-PGF$_1$ refer to the corresponding isomer wherein the 13-olefin double bond is cis and the substituents at the remaining asymmetric centers have configurations opposite to that of the prostaglandin designated by convention as PGE$_1$ or PGF$_1$. Also with respect to the C-8, C-11, C-12, C-13 and C-15 positions, the same number designation will be used regardless of the actual number of carbon atoms in the upper (acid) chain. Accordingly, in describing a compound having a smaller upper chain than prostanoic acid, the term 6-desalkylene will be used to indicate this difference thus, for example, the term 6-desbutylene-9α,11α,15α-trihydroxy-prost-cis-13-enoic acid refers to the compound having the structure:

Similarly, the term 6-homoalkylene will be used to indicate an upper chain length longer than the normal prostanoic acid upper chain length. Thus, for example, the term 6-homoethylene-9α,11α,15α-trihydroxy-prost-cis-13-enoic acid refers to a compound having the structure:

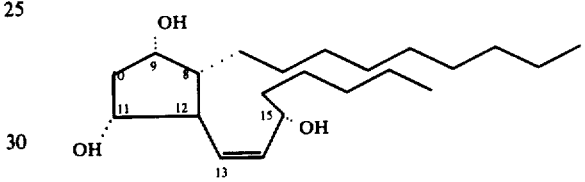

Considering now our process for preparing the octenol ether copper$^{(I)}$ lithium reagent, in greater depth, it is essential that the process be conducted by preparing two distinct sub-component solutions, one containing the octenol ether lithium component and one containing the copper$^{(I)}$ component and then admixing these solutions under controlled conditions. In addition, a particular one of the sub-component solutions must also contain the complexing reagent, depending on the particular complexing agent used.

Accordngly, considering the process in detail, the octenol ether and lithium sub-component solution can be prepared by admixing a suitable alkyl lithium with a suitable iodo octenol ether in a suitable solvent at temperatures in the range of about from $-100°$ to $20°$ C for about from 1 to 60 minutes. Preferably this treatment is conducted at temperatures in the range of about from $-80°$ to $0°$ C for about from 20 to 40 minures. Suitable alkyl lithiums include methyl lithium, ethyl lithium, n-propyl lithium and n-butyl lithium; and preferably n-butyl lithium.

Suitable iodo octenol ethers which can be used either as racemic (dl) mixtures or as the pure (R) or (S) optically active isomer, are those having the formula:

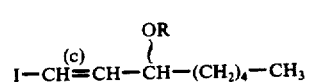

wherein the (c) over the double bond indicates the cis configuration; —OR is selected from the group consisting of acid labile ethers having from 3 through 10 carbon atoms; and the wavy bond line indicates an asymmetric carbon center and indicates both the (dl) racemic mixture or the individual (R) or (S) optically active isomer.

Also, mixtures of the (dl)-1-iodo-cis-1-octen-3-ol 3-ether; (R)-1-iodo-cis-1-octen-3-ol 3-ether and (S)-1-iodo-cis-1-octen-3-ol 3-ether can be used, though typically this would not be desirable as the primary advantage of the optically active (R)- reagent and (S)- reagent is their (stereochemical) selectivity; which would be wasted by mixture with the (dl)-reagent or with each other. Accordingly, the pure (R)-1-iodo-cis-1-octen-3-ol 3-ethers and pure (S)-1-iodo-cis-1-octen-3-ol 3-ethers are preferred. Also, mixtures of different 3-ethers could be used, for example, (S)-1-iodo-3-(2'-methoxyprop-2'-oxy)-cis-1-octene and (S)-1-iodo-3-(tetrahydropyranyl-2'-oxy)-cis-1octene.

The preferred iodo octenol ethers are:

(dl)-1-iodo-3-(2'-methoxyprop-2'-oxy)-cis-1-octene;
(R)-1-iodo-3-(2'-methoxyprop-2'-oxy)-cis-1-octene;
(S)-1-iodo-3-(2'-methoxyprop-2'-methoxyprop-2'-oxy)-cis-1-octene;
(dl)-1iodo-3-(tetrahydroyranyl-2'-oxy)-cis-1-octene;
(R)-1-iodo-3-(tetrahydropyranyl-2'-oxy)-cis-1-octene; and
(S)-1-iodo-3-(tetrahydropyranyl-2'-oxy)-cis-1-octene.

Accordingly because of the isomeric selectivity, the particularly preferred iodo octenol ethers are:

(R)-1-iodo-3-(2'-methoxyprop-2'-oxy)-cis-1-octene;
(S)-1-iodo-3-(2'-methoxyprop-2'-oxy)-cis-1-octene;
(R)-1-iodo-3-(tetrahydropyranyl-2'-oxy)-cis-1-octene;
(S)-1-iodo-3-(tetrahydropyranyl-2'-oxy)-cis-1-octene;
(R)-1-iodo3-methoxymethoxy-cis-1-octene; and
(S)-1-iodo-3-methoxymethoxy-cis-1-octene.

Also, as previously noted, the 3-(2'-methoxyprop-2'-oxy) reagents will yield prostaglandin ether derivatives having very easily cleavable 15-ether groups.

Also, as this treatment and also subsequent treatments can be conducted at substantially reduced temperatures, it is necessary that the inert organic solvent have a melting point below the particular treatment temperature used, to ensure that the liquid state is retained. Suitable solvents include alkane solvents having a melting point below the particular treatment temperature used. Thus, by increasing the treatment temperatures, a slightly broader range of solvents can be used. Suitable alkane solvents which are operable throughout the −100° to 20° C range include, for example, pentane, hexane, heptane and the like. Typically, best results are obtained using hexane.

The copper component solution can be prepared by dissolving a copper$^{(I)}$ halide salt in a suitable inert organic solvent. Typically, the treatment is conducted at about from 0° to 30° C. The particular temperature used is not critical with respect to this treatment, however, as the ultimate mixing step can be conducted at reduced temperatures (i.e. −100° to 20° C) it is necessary that the inert solvent have a melting point below the temperature used in the ultimate mixing step. Suitable solvents include ether solvents having melting points below the temperature used in the ultimate mixing step. Suitable ether solvents include, for example, dielthyl ether, methyl ethyl ether, and the like. Best results are typically obtained using diethyl ether. Suitable copper$^{(I)}$ halides which can be used include copper$^{(I)}$ iodide, copper$^{(I)}$ fluoride, copper$^{(I)}$ chloride, and copper$^{(I)}$ bromide. Best results are obtained using copper$^{(I)}$ iodide. Typically, a copper$^{(I)}$ halide salt solvent concentration in the range of about from 0.5 to 50 wt. %, preferably 2 to 10%, is used, though again this is largely a matter of convenience and concentrations both above and below this can also be used.

As noted above, the complexing reagent must be present, in particular one of the sub-component solutions, prior to their admixture together. Thus, where a combination complexing reagent-copper$^{(I)}$ halide (e.g. bi-(trimethylphosphite)copper$^{(I)}$ iodide) is used, the complexing reagent is inherently present in the copper$^{(I)}$ sub-component solution and the copper component solution can be prepared in the same manner as described above but merely replacing the coppr$^{(I)}$ halide with the combination complexing reagent copper$^{(I)}$ halide.

Where a trialkyl phosphite or trialkyl phosphine complexing reagent is used, the complexing agent is added to the copper$^{(I)}$ halide solution. This addition can take place either before or after the addition of the copper$^{(I)}$ salt to the solvent and typically the copper$^{(I)}$ salt and phosphite or phosphine complex are added at about the same time. Suitable phosphite and phosphine complexing agents include trimethyl phoshite, triethyl phosphite, tri(n-propyl)phoshite, and tri(n-butyl)phosphite; trimethyl phosphine, triethyl phosphine, tri(n-propyl)phosphine, and tri(n-butyl)phosphine. Typically, better results are obtained with the phosphite complexing reagents than the phosphine complexing reagents. The preferred phosphite complexing reagent is trimethyl phosphite and the preferred phosphine complexing reagent is tri(n-butyl)phosphine.

Where a diamine type complexing reagent (e.g. tetraalkylalkylenediamines; naphthalene bridge diamines, alkylpiperazines and the like) is used, the complexing agent is added to the octenol ether lithium solution and must be added to the product solution (i.e. after the addition of the desired alkyl lithium and iodo cis-octenol ether and after the solution has been allowed to stand as described above). In this case, the addition of complexing agent is typically conducted at temperatures in the range of about from −100° to 20° C, preferably in the range of about from −80° to 0° C for about from 20 to 40 minutes. Preferably, the diamine complexing agent is a tetraalkylalklenediamine, as previously described. Best results are typically obtained using N,N,N',N'-tetramethylethylennediamine.

Where the copper$^{(I)}$ iodide solution contains the complexing reagent, the final mixing treatment can be conducted by admixing the octenol ether lithium solution and copper$^{(I)}$ halide solution at temperatures in the range of about from −80° to 0° C for about from 5 minutes to 6 hours. Preferably, the treatment is conducted at a temperature of about −40° C for about from 5 minutes to 6 hours. Also, it is preferable to cool the copper salt solution to the mixing temperature range if it is not already within the temperature range.

Where the octenol ether lithium solution contains the complexing reagent (e.g. diamines), the final mixing treatment can be conducted by adding the octenol ether lithium solution to the copper$^{(I)}$ halide solution at temperatures in the range of about from −100° to 20° C, preferably about from −80° to 0° C. After the initial admixture, the temperature is increased to about from −50° to 0° C, preferably about −20° C and maintained at this temperature for about from 5 minutes to 6 hours, preferably about from 20 to 40 minutes. Also, in this case, the copper$^{(I)}$ halide solution should be precooled to about from −100° to 20° C, preferably about −80° to 0°

C (if it is not already within this temperature range) prior to the solution of the octenol ether lithium solution.

Where a tri(alkyl)phosphite or tri(alkyl)phosphine complexing agent is used, it is preferable to admix respective sub-component solutions in relative proportions to provide an ultimate mixture having the following ratio of components (based on initial starting materials) per mole of iodooctenol ether:

1 mole of alkyl lithium;
0.05 to 2 moles of copper halide;
0.1 to 4 moles of trialkyl phosphite or trialkyl phosphine.

Best results are obtained wherein the final mixture, based on initial starting materials, contains about 1 mole of alkyl lithium; about 0.5 mole of copper$^{(I)}$ halide; and about one mole of trialkyl phosphite or trialkyl phosphine per mole of iodooctenol ether.

Where a tetraalkylalkylenediamine complexing agent is used, the respective solutions should be admixed in relative ratios to provide an ultimate mixture having about the following ratio of components (based on initial starting materials) per mole of iodooctenol ether:

1 mole of alkyl lithium;
0.05 to 2 moles of copper$^{(I)}$ halide;
0.1 to 4 moles of tetraalkylalkylenediamine.

Best results are obtained using about 1 mole of alkyl lithium; about 0.5 mole of copper halide and about from 0.5 to 1 mole of tetraalkylalkylenediamine per mole of iodooctenol ether.

Where bis-(trimethylphosphite) copper$^{(I)}$ iodide is used, it is preferable that the respective solutions are admixed in relative proportions to provide an ultimate mixture having about the following ratio of components (based on initial starting materials) per mole of iodooctenol ether:

1 mole of alkyl lithium;
0.05 to 2 moles of bis-(trimethylphosphite) copper$^{(I)}$ iodide.

Best results are obtained using about one mole of alkyl lithium and about 0.5 mole of bis-(trimethylphosphite) copper$^{(I)}$ iodide per mole of iodooctenol ether.

The process, of the invention, for preparing the 9-oxo-13-cis prostaglandin derivatives of the invention can be schematically represents by the following overall reaction equation:

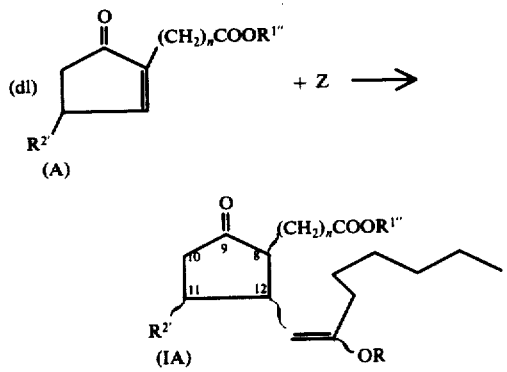

wherein $R^{1''}$ is alkyl having from one through ten carbon atoms, chloroethyl, dichloroethyl or trichloroethyl; $R^{2'}$ is hydrogen or conventional acid labile ether having from three through ten carbon atoms; and Z is the complexed octenol ether copper$^{(I)}$ lithium reagent, of the invention, and OR corresponds to the ether group of said complexed octenol ether copper$^{(I)}$ lithium reagent and the ~ line indicates either the $\alpha$ or $\beta$ configuration or mixtures of isomers having the $\alpha$ and $\beta$ configuration; and the wavy lines at the C-8, C-11 and C-12 positions indicate the $\alpha$ and $\beta$ configuration and wherein the substituents at C-8 and C-12; and C-11 and C-12 are trans to each other (i.e., have opposite configurations).

The process can be effected by treating the appropriate starting material of formula A, having the desired $R^{2'}$ substituent and side chain, with the complexed cis-octenol ether copper$^{(I)}$ lithium reagent of our invention under reactive conditions. The treatment can be conducted at temperatures in the range of about from $-100°$ to $20°$ C, preferably about from $-80°$ to $0°$ C for about from five minutes to 24 hours. Preferably, the treatment is conducted by adding a solution of the cyclopentenone starting material of formula A, in a suitable inert organic solvent, directly to the reagent of our invention. Suitable inert organic solvents include, for example, diethyl ether, methyl ethyl ether and the like. Also, substantially superior results are obtained by using freshly prepared complexed octenol ether copper$^{(I)}$ lithium reagents.

Our process affords the important advantage that the octenyl 3-ether side chain attaches to the cyclopentane moiety at an opposite configuration to the carboalkoxyhexyl side chain (i.e. $\alpha,\beta$ or $\beta,\alpha$), thus enhancing isomer selectivity and eliminating the undesired by-product isomers wherein the side chains have the same configuration, i.e. $\alpha,\alpha$ or $\beta,\beta$ and in addition affords high yields as compared with conventional prostaglandin synthesis.

We have surprisingly found that the use of racemic reagent will typically yield a product which is in effect stereo specific with respect to the C-15 position in contrast to the diastereomeric 15$\alpha$- and 15$\beta$-isomer mixture, which one would expect. Thus, we have found that the use of (dl)-1-iodo-cis-1-octen-3-ol 3-ether derived reagent will yield the corresponding enantiomeric 15$\beta$-ether-13-cis prostanoic acid ester (e.g. formula III) and retro-15$\alpha$-ether-13-cis prostanoic acid ester (e.g. formula IIIr), with no or only negligible quantities of the corresponding 15$\alpha$- and retro-15$\beta$ethers (e.g. formulas IV and IVr). Further, when a pure optically active (R)-iodo-cis-1-octen-3-ol 3-ether or pure optically active (S)-iodo-cis-1-octen-3-ol 3-ether derived reagent is used, the respective products will be single enantiomers. Thus, the optically active (R) reagent will yield the corresponding 15$\beta$-ether-13-cis prostanoic acid ester — i.e. (R)-stereochemistry at C-15 — (e.g. formula III) and the optically active (S) reagent will yield the corresponding retro-15$\alpha$-ether-13-cis prostanoic acid ester — i.e. (S)-stereochemistry at C-15 — (e.g. formula IIIr). Hence, by using a pure optically active (R) or (S) reagent, isomer product mixtures are precluded.

Where other isomeric products are desired (e.g. formula IV and IVr), these products can be obtained by epimerization via solvolysis of the corresponding 15$\beta$- and retro15$\alpha$-ether-13-cis prostanoic acid esters (e.g. formulas III and IIIr), respectively. We have found that in the case of the compounds of formula I wherein $R^2$ is hydrogen that this can be conveniently effected by solvolysis according to the following schematic overall reaction sequence:

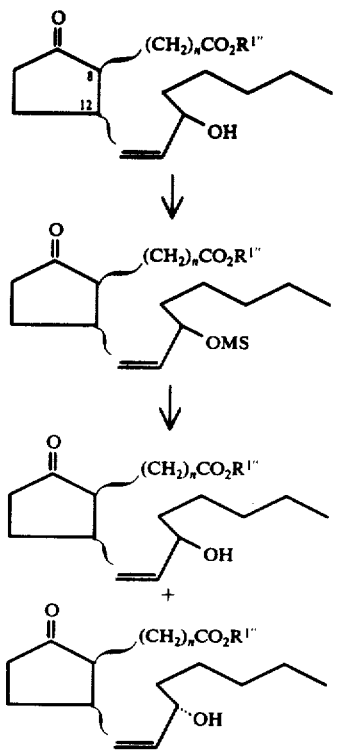

wherein R¹'' is as defined herein above, Ms is methanesulfonyl and the substituents indicated at C-8 and C-12 by the wavy lines are trans to each other.

In the first step of this treatment, the 15β-hydroxy substituent is mesylated or tosylated via any suitable procedure. For example, this can be effected by treatment with methanesulfonyl chloride in a suitable inert organic solvent (e.g. methylene chloride), typically at temperatures in the range of about from $-40°$ to $-5°$ C for about from 10 minutes to 2 hours. Also in place of methanesulfonyl chloride, other lower alkanesulfonyl chlorides or phenylsulfonyl chlorides could also be used. The resulting mixture is then preferably merely allowed to rise to around room temperature, washed with water yielding a two phase water-methylene chloride product fraction. The methylene chloride product fraction is separated and then treated (step 2) with aqueous acetone. This treatment is typically conducted at temperatures in the range of about from 10° to 30° C, conveniently room temperature, for about from two to 48 hours, preferably about 12 to 24 hours. As can be seen from the above reaction equation, the resulting product is a mixture of the corresponding 15α and 15β isomers. The treatment can be applied to both pure enantiomers and mixtures of enantiomers. Typically, the ratio of 15α- to 15β- is in the range of about 40:60 to 60:40. Where a racemic pair of enantiomers is used as the starting material for the solvolysis, the product will be a mixture of two different racemic pairs of enantiomers. Further, variation in the ratio mix can be obtained, if desired, by adding the desired pure 15α or 15β isomers (prepared by the use of optically active reagents as described above) to the product.

Where it is desired to prepare 15α-, 15β-isomer mixtures having a hydroxy function at C-11 (i.e. R² is hydroxy) via this route, it is preferable to prepare a 13-cis prostaglandin having an easily cleavable acid labile ether at C-15 (e.g. OR is 2'-methoxyprop-2'-oxy) and a more stable acid labile ether at C-11 (e.g. R² is tetrahydropyranyl-2'-oxy). The epimerization can then be conducted according to the following schematically represented process:

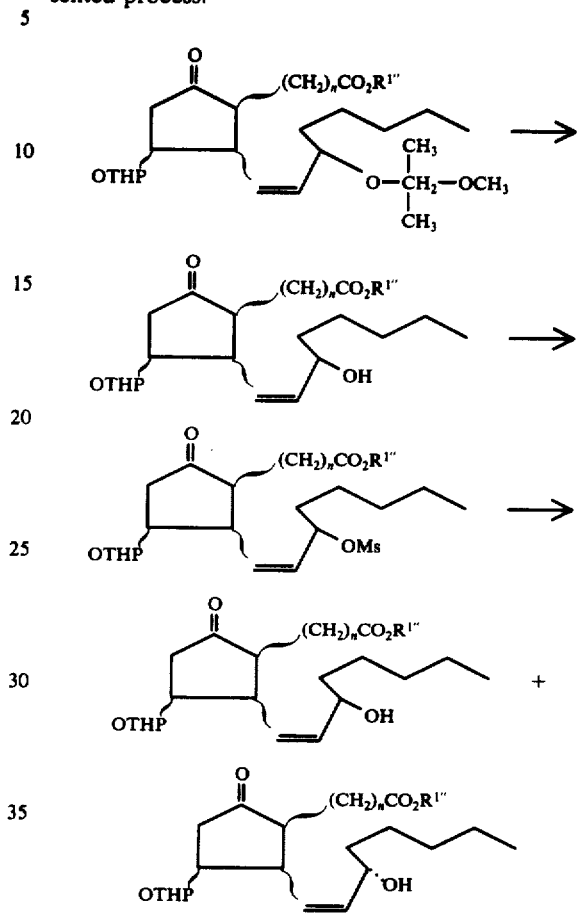

wherein —OTHP is tetrahydropyranyl-2'-oxy; —OMs is methanesulfonyloxy or equivalent group; and R¹'' is as defined herein above.

The first step in this treatment can be effected via any suitable acid hydrolysis treatment sufficiently mild to cleave the ether group at C-15 (shown as methoxypropoxy for convenience) without cleaving the ether group at C-11 (shown as tetrahydropyranyloxy for convenience). In the case of C-15 methoxypropoxy and C-11 tetrahydropyranyloxy, this can be conveniently effected by treatment with aqueous acetic acid (typically 10 to 25% wt.) at about from 0° to 40° C, typically at room temperature, for about from 1 to 60 minutes. The remaining steps (i.e. mesylation and solvolysis) can be conducted as described above with respect to the C-11 hydrogen (R² is hydrogen) 13-cis prostaglandin derivatives.

The PGF series of the 13-cis prostaglandin derivatives of formula I can be prepared via reduction of the corresponding PGE (R³ is oxo)-13-cis prostaglandin derivatives:

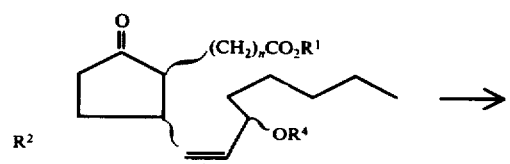

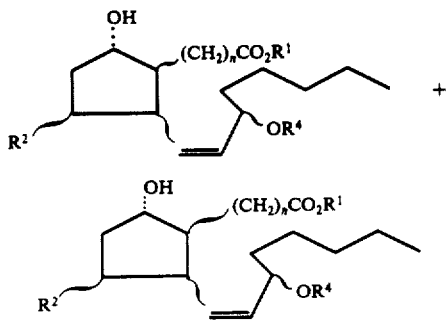

wherein R[1], R[2] and OR[4] and the wavy lines are as defined herein above.

The respective 9,15-dihydroxy-prost-13-enoic acids and lower alkyl esters can be prepared by reducing the corresponding 9-oxo function to the corresponding 9-hydroxy function. This can be conveniently effected by treatment with sodium borohydride in a suitable inert organic solvent (e.g. methanol). Typically this treatment is conducted at temperatures in the range of about from 0° to 25° C for about from 1 to 10 hours. Also in place of methanol, other suitable solvents which can be used include, for example, tetrahydrofuran, dioxane, etc., and the like. Since the reduction is not selective, the number of isomers in the product reaction mixture will be double that in the starting material because of the introduction of the asymmetric center at C-9. Thus, where pure 15-α-hydroxy or 15-β-hydroxy starting materials are used, the resulting product will be a mixture of the corresponding 9α- and 9β-hydroxy epimers. The resulting pure 9α- and 9β-hydroxy epimers can be separated according to conventional procedures such as, for example, column chromatography. Thus, where pure enantiomers are desired, it is preferable to use pure enantiomer starting materials in order to minimize the number of enantiomer products and facilitate separation.

The respective acid labile ether groups at C-11 and/or C-15 can be removed by conventional mild acid hydrolysis. Thus, for example, the ether groups can be conveniently removed via treatment with 50 to 75% wt. aqueous acetic acid at temperatures in the range of about from 15° to 50° C, conveniently room temperature, for about from 5 to 48 hours. The acids (i.e. R[1] is hydrogen) of formula I can be prepared by cleaving the corresponding R[1]-esters. This can be conveniently effected via any suitable microbiological enzymatic procedure for cleaving ester groups. A preferred non-limiting enzymatic hydrolysis procedure is, for purposes of illustration, described herein below in Example 10.

Throughout the above described processes where pure optically active isomeric products are described, it is preferable to use the appropriate optically active (R) or (S) reagents and to conduct the various substituent modifications in a sequence to obtain pure enantiomeric products or diastereomeric products as contrasted to racemic products; since the respective diastereomeric isomers can be separated by relatively simple procedures, e.g. chromatography, in contrast to the more difficult and complex procedures required to separate racemic mixtures. Illustrations of typical non-limiting diastereomeric separation procedures can be had by reference to the appropriate Examples set forth herein below.

Because of the high yields of 13-cis prostaglandin products, which are obtained by our process, we have found that by subsequently rearranging the 13-cis double bond that we have obtained a felicitous process for preparing prostaglandin products having the natural 13-trans orientation. This process can be represented by the following schematic reaction sequence:

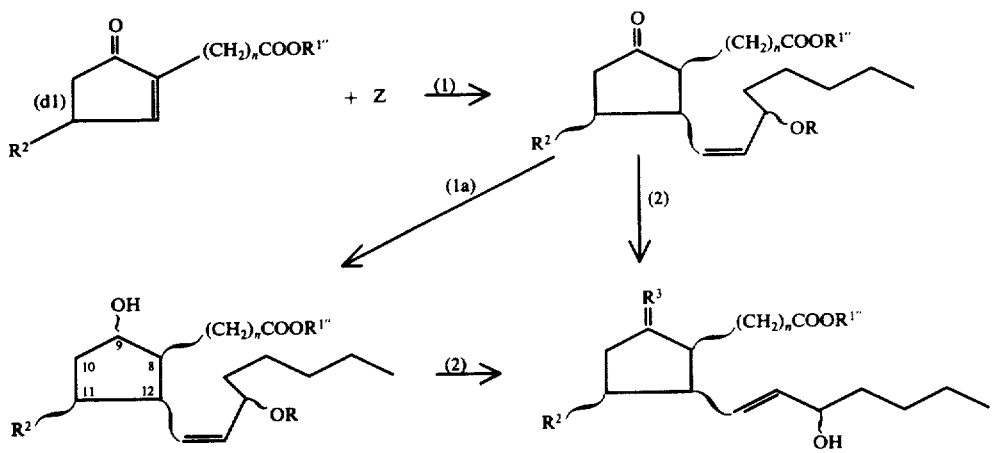

wherein $n$, R[1'''], R[2], R[3], OR and the wavy lines are as defined herein above.

Step 1, the initial preparation of the 9-oxo-13-cis prostanoic acid derivation, is conducted as previously described. Where the PGF series is desired, the oxo group can be reduced to a hydroxy group via step 1a which can be conducted as previously described. The reduction step can be conducted either before or after the rearrangement step (2). The rearrangement step (step 2) can be conducted according to conventional rearrangement steps and is generally easily effected since the 13-trans orientation is the favored orientation and is in fact the orientation which occurs in nature. The rearrangement can, for example, be conveniently effected by treating the corresponding 13-cis prostenoic acid, or preferably an ester thereof, with a suitable free radical initiator (e.g. diphenyldisulfide) in a suitable inert organic solvent (e.g. benzene) and irradiation with visible wave length light (e.g. conventional sun lamp). In the case of the 11-hydroxy-13-cis prostenoic acids (preferably esters), it is preferable to first protect the 11-hydroxy substituents, and any other hydroxy substituents which are present, with a tetrahydropyranyloxy group, or other suitable ether groups, prior to rearrangement (step 2). The ether and ester groups can then be cleaved, if desired, in the same manner as described herein above with respect to the 13-cis prostaglandin acid derivatives.

STARTING MATERIALS

The 1-idod-cis-1-octen-3-ol 3-ethers, used in the preparation of the reagent, of the invention, can be prepared by the following schematically represented overall reaction equation sequence:

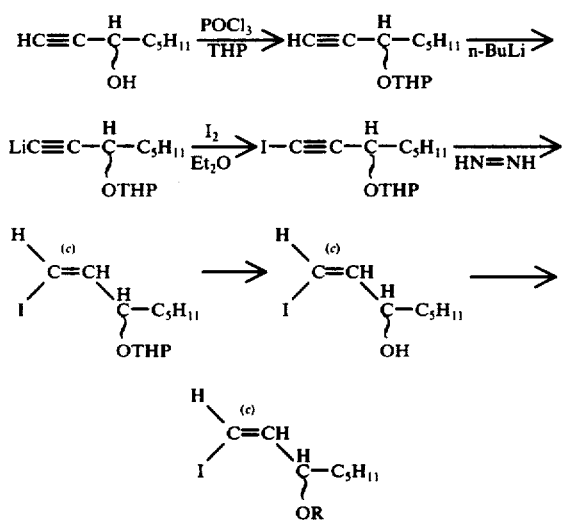

wherein OR is as defined herein above; the wavy line indicates either the optically (R) or (S) isomer or a racemic mixture thereof; and the (c) over the double bond indicates the cis configuration.

The (S)-1-octyn-3-ol starting materials can be prepared by known procedures such as, for example, described by Fried et al. in *Ann. N.Y. Acad. Sci.*, v. 180, p. 38 (1971). The (R)-1-octyn-3-ol starting material can be prepared according to the same procedure by using the (+)-α-phenethylamine in place of (−)-α-phenethylamine.

The starting materials of formula A wherein $R^2$ is hydrogen can be conveniently prepared according to the following schematic overall reaction equation sequence:

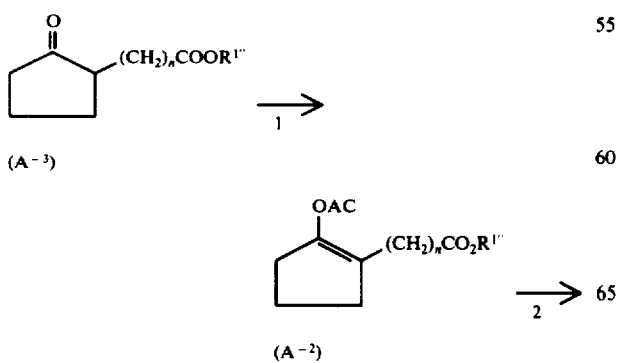

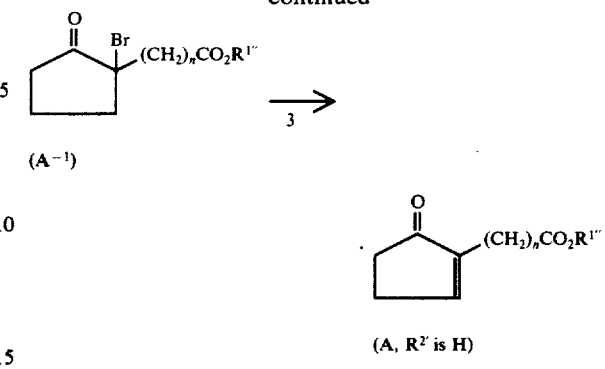

wherein $R^{1''}$ and $n$ are as defined above; and Ac is a conventional labile acyl, preferably acetyl.

Step 1 of the above preparation can be conveniently effected by treating the compounds of formula $A^{-3}$ with isopropenyl acetate in the presence of an acid catalyst. This treatment should be conducted under anhydrous conditions and is typically conducted at the boiling point of isopropenyl acetate until the reaction is complete, usually from three to twelve hours. Typically, a large excess of isopropenyl acetate is used. Also in place of isopropenyl acetate, other suitable reagents can be used, for example, acetic anhydride, propionic anhydride and the like. Suitable acid catalysts which can be used include, for example, mineral acids such as, for example, sulfuric acid and the like and organic acids such as, for example, p-toluenesulfonic acid or oxalic acid. The compounds of formula $A^{-3}$ are known compounds or can be prepared according to known procedures. For example, compounds of formula A can be prepared by the general procedure described by Bagli et al. in *Tetrahedron Letters*, 465-470 (1966), but substituting a bromocarboxylic ester of the appropriate chain length in place of ethyl ω-bromoheptanoate where a starting material, of formula $A^{-3}$, is desired having a chain length other than $n$ is 6 is desired.

Step 2 of our preparation is conveniently effected by treating the compounds of formula $A^{-2}$ with N-bromoacetamide or N-bromosuccinimide in a suitable inert organic solvent. Typically, this step is conducted at temperatures in the range of about from −10° to 25° C for about from 5 minutes to 3 hours. Preferably the reaction solution is monitored, for example, by thin-layer chromatography, to ensure that the starting material of formula $A^{-2}$ is consumed before starting the third step. In step 3, the initial reaction mixture is treated with a suitable base such as, for example, lithium carbonate in pyridine. This phase is typically conducted at temperatures in the range of about from 50° to 100° C for about from 1 to 5 hours.

Alternatively, this treatment can be effected via the use of molecular bromine, in the first phase, in a suitably inert solvent such as, for example, methylene chloride, chloroform, dioxane, carbon tetrachloride and the like. Typically, temperatures in the range of about −10° to 25° C will be used.

The starting materials of formula (A) wherein $R^2$ is a conventional labile ether group can be conveniently prepared according to the following schematic overall reaction sequence:

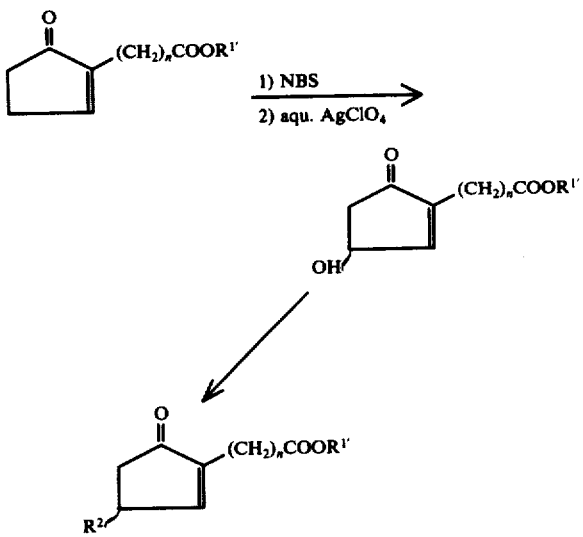

wherein R[1'] and the wavy lines are as defined herein above; and R[2'] is an acid labile ether having from three through ten carbon atoms.

The first step of this process is conveniently conducted in two phases and can be conveniently effected by treating the desired 2-(carboalkoxy-alkyl)-1-oxo-cyclopent-2-ene with N-bromosuccinimide or equivalent reagent (e.g. N-bromoacetamide, N,N-dibromoacetamide, etc.) in a suitable inert organic solvent (e.g. carbon tetrachloride) followed by irradiation of the mixture with visible wave length light and then treating the product with silver perchlorate in a suitable aqueous inert organic solvent. Considering this treatment as two phases, the first phase is typically conducted at temperatures in the range of about from 0° C to the boiling point of the solvent for about from ½ to 2 hours. Suitable inert organic solvents which can be used include, for example, carbon tetrachloride, and the like. Typically, a mole ratio in the range of about from slightly above 1.2 moles of N-bromosuccinimide per mole of cyclopentenone derivative starting material is used.

With respect to the irradiation light, any suitable source of visible light can be used, for example, conventional sun lamps.

The second phase of this step can be conveniently effected by treating the brominated product of the first phase with silver perchlorate in a suitable aqueous inert organic solvent. Typically, this phase is conducted at temperatures in the range of about from 0° to 80° C, preferably about from 10° to 35° C for about from ½ to 2 hours. Suitable aqueous inert organic solvents which can be used include, for example, aqueous acetone, aqueous tetrahydrofuran, aqueous dioxane, and the like. Also, preferably the crude brominated product is separated from the first phase reaction mixture prior to conducting the second phase.

The next step, the addition of the ether group, can be effected via any suitable procedure for selectively protecting a hydroxy group, in preference to an oxo group, with the desired ether group. Thus, for example, this can be conveniently obtained by treating the 2-(carboalkoxy-alkyl)-4-hydroxy-1-oxo-cyclopent-2-ene product with the desired ether (e.g. isopropenyl methyl ether, dihydropyran, etc.) in the presence of an acid catalyst (e.g. phosphorous oxychloride, p-toluenesulfonic acid, etc.). Typically, this treatment is conducted at temperatures in the range of about from 15° to 30° C, conveniently at room temperature for about from ½ to 4 hours. Optionally, an inert organic solvent can also be used, though the ether reagent will itself also serve as solvent.

Isolation of the intermediates and products can be effected by any suitable separation or purification procedure such as, for example, extraction, filtration, evaporation, crystallization, and thin-layer chromatography. Specific illustrations of typical separation and isolation procedures can be had by reference to the examples described herein below. However, other equivalent separation or isolation procedures could, of course, also be used.

The prostaglandin products and prostaglandin derivative products of the above processes exhibit prostaglandin-like biological activities and thus are useful in the treatment of mammals where the use of prostaglandins are indicated. The compound (and pharmaceutically acceptable salts) are bronchodilators and thus are useful in treating mammals for bronchial spasm or wherever strong bronchodilators are indicated. The compounds are also useful in controlling or palliating hypertension in mammals and further exhibit central nervous system depressant activity, in mammals, and are useful as sedatives. In addition, the compounds are useful for inducing labor, in pregnancy, and for inducing menses to correct or reduce menstrual abnormalities. The compounds also possess anti-fertility properties. The 13-cis compounds also exhibit anti-inflammatory activities and thus are useful as anti-inflammatory agents.

These compounds can be administered in a wide variety of dosage forms, either alone or in combination with other pharmaceutically compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid, or aerosol, in which the compound and/or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspension, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, talcum, sodium bisulfite and the like.

For inhalation administration, the compounds can, for example, be administered as an aerosol comprising the compounds or salts in an inert propellant together with a cosolvent (e.g. ethanol) together with optional preservatives and buffering agents. Additional general information concerning the inhalation administration of aerosols can be had by reference to U.S. Pat. Nos. 2,868,691 and 3,095,355.

The compounds are typically administered in dosages of about from 0.1 to 10 mg. per kg. of body weight. The precise effective dosage will, of course, vary depending upon the mode of administration, condition being treated, and host.

A further understanding of the invention can be had from the following non-limiting preparations and examples. Also, where necessary, preparations and examples are repeated to provide starting materials for subsequent preparations and examples.

PREPARATION 1

This preparation illustrates methods for preparing (dl)-1-iodo-cis-1-octen-3-ol. In this preparation 22 ml. of 1.5M n-butyl lithium in hexane is added to a mixture containing 6.3 g. of (dl)-3-(tetrahydropyranyl-2'-oxy)-1-octyne (prepared by the acid catalyzed treatment of (dl)-1-iodo-1-octyn-3-ol with dihydropyran), in 100 ml. of diethyl ether at −78° C, under a nitrogen atmosphere, with constant stirring. After 30 minutes a mixture containing 15 g. of iodine in 70 ml. of diethyl ether is added and the resulting mixture warmed to room temperature. The mixture is then treated with 5% aqueous sodium thiosulfate solution to consume excess iodine, resulting in the formation of a two phase liquid-liquid system. The ether layer is separated and washed with saturated aqueous sodium chloride solution and then evaporated to dryness, under vacuum, yielding a crude residue of (dl)-1-iodo-3-(tetrahydropyranyl-2'-oxy)-1-octyne. The residue is dissolved in 100 ml. of methanol and added to 20 g. of dipotassium azodicarboxylate. Fifteen milliliters of acetic acid is slowly added dropwise over a period of about 1 hour. The reaction mixture is monitored by vapor phase chromatography to ensure that the reaction has gone to completion and the filtered and concentrated by vacuum evaporation to a volume of approximately 30 ml. The concentrate is poured into 300 ml. of water and the resulting mixture extracted with four 50 ml. portions of diethyl ether. The ether extracts are combined and evaporated to dryness under vacuum. The residue is stirred for 16 hours with 20 ml. of a 40% aqueous dimethylamine mixture and then poured into 100 g. of ice yielding a two phase liquid-liquid mixture. The aqueous phase is made slightly acid by the addition of 4M aqueous hydrochloric acid. The mixture is then extracted with four 50 ml. portions of diethyl ether. The ether extracts are combined and shaken with 50 ml. of aqueous saturated sodium chloride solution, and then evaporated under vacuum to remove the ether solvent. The resulting residue is stirred with 40 ml. of aqueous 65% dichloro acetic acid for two hours at room temperature and then poured onto 100 g. of ice. The mixture is then made slightly basic by the controlled addition of aqueous 15% sodium hydroxide solution and extracted with four 50 ml. portions of diethyl ether. The ether extracts are combined and concentrated by vacuum evaporation affording a residue which is chromatographed over a mixture containing 250 g. of silica gel and 5 g. of powered copper, eluting with 10% ethyl acetate-hexane mixtures, yielding (dl)-cis-1-octen-3-ol.

Similarly (R)-1-iodo-cis-1-octen-3-ol and (S)-1-iodo-cis-1-octen-3-ol are respectively prepared according to the same procedure but respectively replacing (dl)-3-(tetrahydropyranyl-2'-oxy)-1-octyne with (R)-3-(tetrahydropyranyl-2'-oxy)-1-octyne and (S) -3-(tetrahydropyranyl-2'-oxy)-1-octyne.

PREPARATION 2

This preparation illustrates additional methods of preparing 3-ethers of (dl)-; (R)- and (S)-1-iodo-cis-1-octen-3-ol. In this example a small drop of phosphorous oxychloride is added to a mixture containing 2.71 g. of (dl)-1-iodo-cis-1-octen-3-ol and 5 g. of isopropenyl methyl ether. The mixture is maintained in a closed reaction vessel for 45 minutes at room temperature an then three drops of triethylamine is added and the resulting mixture evaporated by vacuum evaporation affording a residue of pure (dl)-1-iodo-3-(2'-methoxyprop-2'-oxy)-cis-1-octene.

Similarly, by following the same procedure but respectively using n-butyl isopropenyl ether and pentylcyclohexenyl ether in place is isopropenyl methyl ether, the following compounds are respectively prepared:

(dl)-1-iodo-3-(2'-butoxyprop-2'-oxy)-cis-1-octene; and
(dl)-1-iodo-3-(1'-pent-1"-oxycyclohexyl-1'-oxy)-cis-1-octene.

Similarly, by following the same procedure but respectively replacing (dl)-1-iodo-cis-1-octen-3-ol with (R)-1-iodo-cis-1-octen-3-ol and (S)-1-iodo-cis-1-octen-3-ol, the following optically active compounds are respectively prepared:

(R)-1-iodo-3-(2'-methoxyprop-2'-oxy)-cis-1-octene;
(S)-1-iodo-3-(2'-methoxyprop-2'-oxy)-cis-1-octene;
(R)-1-iodo-3-(2'-butoxyprop-2'-oxy)-cis-1-octene;
(S)-1-iodo-3-(2'-butoxyprop-2'-oxy)-cis-1-octene;
(R)-1-iodo-3-(1'-pent-1"-oxycyclohexyl-1'-oxy)-cis-1-octene; and
(S)-1-iodo-3-(1'-pent-1"-oxycyclohexyl-1'-oxy)-cis-1-octene.

PREPARATION 3

This preparation illustrates further methods of preparing 3-ethers of (dl)-; (R) and (S)-1iodo-cis-1-octen-3-ol. In this example 5.05 g. of a 56% (wt.) dispersion of sodium hydride in mineral oil is washed with two 100 ml. portions of pentane, followed by decantation to remove excess pentane. 125 Ml. of tetrahydrofuran is then added and the resulting mixture is maintained under nitrogen. A solution containing 25.4 g. of (dl)-1-iodo-cis-1-octen-3-ol in 125 ml. of anhydrous tetrahydrofuran is then slowly added over a 30 minute period and the resulting mixture refluxed for an additional 30 minutes. After this time a solution containing 12.5 g. of 2-chlorotetrahydropyran in 50 ml. of anhydrous tetrahydrofuran is slowly added over a 15 minute period and the resulting mixture refluxed for an additional hour, and then cooled to room temperature and added to 500 ml. of water, followed by extraction with three 100 ml. portions of diethyl ether. The combined diethyl ether fractions are dried over potassium carbonate, filtered, and the resulting filtrate evaporated to dryness affording a crude residue of (dl)-1-iodo-3-(tetrahyropyranyl-2'-oxy)-cis-1-octene, which is then further purified by chromatography on 1,000 g. of silica gel eluting with 20% ether-hexane mixture.

Similarly, the respectively replacing 2-chlorotetrahydropyran with α-chloroethyl phenyl ether and α-chloroethyl ethyl ether, the following compounds are respectively prepared:

(dl)-1-iodo-3-α-phenoxyethoxy-cis-1-octene; and (dl)-1-iodo-3-(1'-ethoxyethoxy)-cis-1-octene.

Similarly, by following the same procedure but respectively using (B)-1-iodo-cis-1-octen-3-ol and (S)-1-iodo-cis-1-octen-3-ol in place of (dl)-1-iodo-cis-1-octen-3-ol, the following optically active compounds are respectively prepared:
(R)-1-iodo-3(tetrahydropyranyl-2'-oxy)-cis-1-octene;
(S)-1-iodo-3-(tetrahydropyranyl-2'-oxy)-cis-1-octene;
(R)-1-iodi-3-α-phenoxyethoxy-cis-1-octene;
(S)-1-iodo-3-α-phenoxyethoxy-cis-1-octene;
(R)-1-iodo-3-(1'-ethoxyethoxy)-cis-1-octene; and
(S)-1-iodo-3-(1'-ethoxyethoxy)-cis-1-octene.

PREPARATION 4

This preparation illustrates methods for preparing 1-acyloxy-2-(carboalkoxy-alkyl)-cyclopent-1-ene. In this example, 26.5 g. of 2-(6-carbomethoxy-hexyl)-1-oxo-cyclopentane is added to 250 ml. of isopropenyl acetate containing 0.4 ml. of concentrated sulfuric acid. The mixture is then slowly distilled for 2½ hours and then cooled to room temperature and poured into an ice saturated solution of aqueous sodium bicarbonate. The mixture is then extracted with methylene chloride. The methylene chloride extract is washed with water and then washed with saturated brine, then dried over anhydrous sodium sulfate and evaporated to dryness affording a crude residue of 1-acetoxy-2-(6-carbomethoxyhexyl)-cyclopent-1-ene, which is further purified by high vacuum distillation.

Similarly, by following the same procedure but respectively using the corresponding 2-(carboalkoxy-alkyl)-1-oxocyclopentane starting materials, the following compounds are respectively prepared:

1-acetoxy-2-(6-carboethoxy-hexyl)-cyclopent-1-ene;
1-acetoxy-2-(6-carbohexoxy-hexyl)-cyclopent-1-ene;
1-acetoxy-2-(2-carbomethoxy-ethyl)-cyclopent-1-ene;
1-acetoxy-2-(2-carboethoxy-ethyl)-cyclopent-1-ene;
1-acetoxy-2-(2-carbohexoxy-ethyl)-cyclopent-1-ene;
1-acetoxy-2-(8-carbomethoxy-octyl)-cyclopent-1-ene;
1-acetoxy-2-(8-carboethoxy-octyl)-cyclopent-1-ene; and
1-acetoxy-2-(8-carbohexoxy-octyl)-cyclopent-1-ene.

PREPARATION 5

This preparation illustrates methods of preparing 2-(carboalkoxy-alkyl)-1-oxo-cyclopent-2-ene. In this example 20.1 g. of crude 1-acetoxy-2-(6-carbomethoxy-hexyl)-cyclopent-1-ene, prepared according to Preparation 4, is dissolved in 180 ml. of tetrahydrofuran and 20 ml. of water and then cooled to 0° C under nitrogen. Eleven grams of N-bromoacetamide is added. The resulting reaction solution is monitored by thin-layer chromatography and allowed to stand until complete reaction is indicated. The reaction mixture is then poured into water and extracted with methylene chloride. 150 Milliliters of pyridine and 3 g. of lithium carbonate are added to the methylene chloride extract and the resulting mixture then concentrated by evaporation under reduced pressure to remove most of the methylene chloride. The concentrate is stirred at 90° C under nitrogen, for 1 hour and then examined by thin-layer chromatography to ensure complete reaction. The reaction solution is then cooled to room temperature and poured into water and extracted with methylene chloride. The methylene chloride extract is washed with water, washed with saturated aqueous sodium chloride, then dried over sodium sulfate, and evaported to dryness affording a crude residue of 2-(6-carbomethoxy-hexyl)-1-oxo-cyclopent-2-ene, which is further purified by high vacuum distillation. This product is then dissolved in 350 ml. of methanol, and a solution containing 4.6 g. of semicarbazone hydrochloride and 5 g. of pyridine in 40 ml. of water is then added. The resulting mixture is stirred at room temperature for two hours and then poured into water. The water mixture is filtered, and the collected precipitate is washed with hexane. The filtrate and washings are combined and extracted four times with hexane. The extracts are combined and washed with water, washed with saturated aqueous sodium chloride solution, and then dried over sodium sulfate and evaporated to dryness affording pure 2-(6-carbomethoxy-hexyl)-1-oxo-cyclopent-2-ene.

Similarly, by following the same procedure but respectively using the corresponding products of Preparation 4 as starting materials, the following compounds are respectively prepared:

2-(6-carboethoxy-hexyl)-1-oxo-cyclopent-2-ene;
2-(6-carbohexoxy-hexyl)-1-oxo-cyclopent-2-ene;
2-(2-carbomethoxy-ethyl)-1-oxo-cyclopent-2-ene;
2-(2-carboethoxy-ethyl)-1-oxo-cyclopent-2-ene;
2-(2-carbohexoxy-ethyl)-1-oxo-cyclopent-2-ene;
2-(8-carbomethoxy-octyl)-1-oxo-cyclopent-2-ene;
2-(8-carboethoxy-octyl)-1-oxo-cyclopent-2-ene; and
2-(8-carbohexoxy-octyl)-1-oxo-cyclopent-2-ene.

PREPARATION 6

This preparation illustrates methods of preparing 4-ethers of 2-(carboalkoxy-alkyl)-1-oxo-cyclopent-2-ene. In this example a mixture containing 4.23 g. of 2-(6-carbomethoxy-hexyl)-1-oxo-cyclopent-2-ene and 3.36 g. of N-bromosuccinimide in 100 ml. of carbon tetrachloride is irradiated with visible light (using a 150 watt Photo-Flood lamp) for 20 minutes at 0° C under nitrogen. The mixture is allowed to cool to room temperature and then filtered and the resulting filtrate evaporated, under vacuum, to dryness. Fifty milliliters of a 1:1, by vol., acetone-water mixture containing 5 g. of silver perchlorate is then added to the residue and the resulting mixture allowed to stand for about 20 minutes at room temperature. The mixture is concentrated by evaporation under reduced pressure to remove most of the acetone and the resulting concentrate extracted four times with 100 ml. portions of ethyl acetate. The etyl acetate extracts are combined and sequentially washed with 30 ml. of 5% aqueous sodium bicarbonate solution and 30 ml. of saturated aqueous sodium chloride solution. The ethyl acetate solvent is then removed by evaporation, under vacuum, affording a residue which is further purified by silica gel column chromatography, eluting with ethyl acetate-hexane mixture, yielding pure (dl)-2-(6-carbomethoxy-hexyl)-4-hydroxy-1-oxo-cyclopent-2-ene.

240 Milligrams of 2-(6-carbomethoxy-hexyl)-4-hydroxy-1-oxo-cyclopent-2-ene is dissolved in 5 ml. of benzene containing 200 mg. of isopropenyl methyl ether at room temperature. A small drop of phosphorous oxychloride is added and the resulting mixture is allowed to stand for two hours at room temperature. A drop of triethylamine is then added and the resulting mixture is poured into water and extracted with benzene. The benzene extract is sequentially washed with water and saturated aqueous sodium chloride, dried over sodium sulfate and evaporate, under vacuum, to remove excess solvent yielding a residue of (dl)-2-(6-carbomethoxy-hexyl)-4-(2'-methoxyprop-2'-oxy)-1-oxo-cyclopent-2-ene.

Similarly, by following the same procedure but using the corresponding 2-(carboalkoxy-alkyl)-cyclopent-2-ene products of Preparation 5 as starting materials, the following compounds are respectively prepared:

(dl)-2-(6-carboethoxy-hexyl)-4-(2'-methoxyprop-2'-oxy)-1-oxo-cyclopent-2-ene;
(dl)-2-(6-carbohexoxy-hexyl)-4-(2'-methoxyprop-2'-oxy)-1-oxo-cyclopent-2-ene;
(dl)-2-(2-carbomethoxy-ethyl)-4-(2'-methoxyprop-2'-oxy)-1-oxo-cyclopent-2-ene;
(dl)-2-(2-carboethoxy-ethyl)-4-(2'-methoxyprop-2'-oxy)-1-oxo-cyclopent-2-ene;
(dl)-2-(2-carbohexoxy-ethyl)-4-(2'-methoxyprop-2'-oxy)-1-oxo-cyclopent-2-ene;
(dl)-2-(8-carbomethoxy-octyl)-4-(2'-methoxyprop-2'-oxy)-1-oxo-cyclopent-2-ene;
(dl)-2-(8-carboethoxy-octyl)-4-(2'-methoxyprop-2'-oxy)-1-oxo-cyclopent-2-ene; and
(dl)-2-(8-carbohexoxy-octyl)-4-(2'-methoxyprop-2'-oxy)-1-oxo-cyclopent-2-ene.

Similarly, by following the same procedure as above but respectively replacing isopropenyl methyl ether with isopropenyl ethyl ether, the corresponding 4-(2'-ethoxyprop-2'-oxy) ether analogs of each of the above products is respectively prepared.

PREPARATION 7

This preparation illustrates methods of preparing 4-tetrahydropyranyl ethers 2-(carboalkoxy-alkyl)-1-oxo-cyclopent-2-ene. In this preparation, 2.6 g. of 2-(6-carbomethoxy-hexyl)-4-hydroxy-1-oxo-cyclopent-2-ene is dissolved in 50 ml. of benzene containing 2 ml. of dihydropyran at room temperature. A small drop of phosphorous oxychloride is added and the resulting mixture is stirred for 1½ hours. A drop of triethylamine is then added and the resulting mixture is poured into water and then extracted with benzene. The benzene extract is sequentially washed with water and saturated aqueous sodium chloride, then dried over anhydrous sodium sulfate and evaporated, under vacuum, to remove excess solvent affording a residue of (dl)-2-(6-carbomethoxy-hexyl)-4-(tetrahydropyranyl-2'-oxy)-1-oxo-cyclopent-2-ene, which is further purified by chromatography on silica gel eluting with graduated mixtures of ethyl acetate and hexane.

Similarly, by following the same procedure but using the corresponding 2-(carboalkoxy-alkyl)-1-oxo-cyclopent-2-ene precursors as starting materials, the following compounds are respectively prepared:

(dl)-2-(6-carboethoxy-hexyl)-4-(tetrahydropyranyl-2'-oxy)-1-oxo-cyclopent-2-ene;
(dl)-2-(6-carbohexoxy-hexyl)-4-(tetrahydropyranyl-2'-oxy)-1-oxo-cyclopent-2-ene;
(dl)-2-(2-carbomethoxy-ethyl)-4-(tetrahydropyranyl-2'-oxy)-1-oxo-cyclopent-2-ene;
(dl)-2-(2-carboethoxy-ethyl)-4-(tetrahydropyranyl-2'-oxy)-1-oxo-cyclopent-2-ene;
(dl)-2-(2-carbohexoxy-ethyl)-4-(tetrahydropyranyl-2'-oxy)-1-oxo-cyclopent-2-ene;
(dl)-2-(8-carbomethoxy-octyl)-4-(tetrahydropyranyl-2'-oxy)-1-oxo-cyclopent-2-ene;
(dl)-2-(8-carboethoxy-octyl)-4-(tetrahydropyranyl-2'-oxy)-1-oxo-cyclopent-2-ene; and
(dl)-2-(8-carbohexoxy-octyl)-4-(tetrahydropyranyl-2'-oxy)-1-oxo-cyclopent-2-ene.

PREPARATION 8

This preparation illustrates methods of preparing a pancreatic lipase preparation which can be used to cleave ester groups from prostanoic acid esters. In this preparation; 10 g. of crude pancreatic lipase (note; *Biochem. Biophysics Acta.,* v. 23, page 264 (1957)) is suspended in 65 ml. of water at 0° C. The suspension is stirred for one hour at 0° C and then centrifuged for 20 minutes at 10,000 × g. The supernatant liquid is separated and maintained at 0° C for later use. The precipitate is again suspended in 65 ml. of water at 0° C and centrifuged as before. The supernatant liquid is separated and combined with the previously obtained supernatant liquid and then added to 130 ml. of saturated aqueous ammonium sulfate solution at 0° C, with stirring, and then allowed to stand for 5 minutes. The resulting mixture is then centrifuged at 10,000 × g. for 20 minutes. The supernatant liquid is decanted and the precipitate is collected, then dissolved in sufficient water to yield 125 ml. of solution. Fifteen milliliters of saturated aqueous ammonium sulfate solution is then added to the water solution yielding a suspension which is then centrifuged at 10,000 × g. for 20 minutes. The supernatant liquid is collected and treated with 100 ml. of saturated ammonium sulfate affording a second suspension, which is divided into two equal portions. Each portion is again centrifuged for 20 minutes at 10,000 × g., and in each instance the supernatant liquid is discarded (decantation) and the precipitate collected. Each precipitate is stored at 40° C. prior to use.

The pancreatic lipase ester cleaving preparation is then prepared immediately prior to use by dissolving one of the above precipitates in 25 ml. of an aqueous 0.1 mole sodium chloride and 0.05M calcium chloride solution and then adjusting the pH to 7.2 by the careful addition (i.e. titration) of 0.1M aqueous sodium hyroxide solution.

EXAMPLE 1

This example illustrates methods, according to the invention, of preparing the reagents and compounds of the invention. In this example 6.7 ml. of a 1.5M n-butyl lithium in hexane solution is admixed to a mixture containing 3.26 g. of (dl)-1-iodo-3-(2'-methoxyprop-2'-oxy)-cis-1-octene in 8 ml. of hexene at −78° C under an argon atmosphere. The resulting mixture is stirred and maintained at −78° C, under argon, for 30 minutes. During this time a second mixture containing 2.4 g. of bis-trimethylphosphite copper $^{(I)}$ iodide in 60 ml. of diethyl ether is prepared and maintained under argon and cooled to −78° C. At the end of the 30 minute period, previously referred to, the first mixture is admixed to the second mixture and the temperature of the resulting mixture is brought to −50° C. The resulting mixture is periodically monitored by a Gilman test [note; Gilman and Schulze, *J. Am. Chem. Soc.,* v. 47, 2002 (1925)], and maintained at −50° C until a negative Gilman test is obtained (about 45 minutes). This mixture (a reagent of our invention) is then cooled to −78° C and 1.1 g of 2-(6-carbomethoxy-hexyl)-1-oxo-cyclopent-2-ene in 3 ml. of diethyl ether is added. The resulting mixture is stirred at 78° C for 2.5 hours yielding a (dl)-15β-(2'-methoxyprop-2'-oxy)-9-oxo-prost-13-cisenoic acid methyl ester rich mixture. This mixture is poured into 100 ml. of 20% aqueous acetic acid and stirred at room temperature for 30 minutes yielding a two phase liquid-liquid mixture. The ether layer is separated and extracted with 5% aqueous sodium bicarbonate solution until the aqueous solution is slightly basic. The ethyl ether is then removed by vacuum evaporation and the resulting residue is stirred at room temperature for 30 minutes with 100 ml. of 15% aqueous ammonia and then extracted with two 50 ml. portions of diethyl ether. The diethyl ether extracts are combined and evaporated under vacuum affording a residue which is then chromatographed over 60 g. of silica gel eluting with gradient mixtures of 15% (vol.) ethyl acetate-85% hexane to 50% (vol.) ethyl acetate-50% hexane, yielding (dl)-15$\beta$-hydroxy-9-oxo-prost-13-cis-enoic acid methyl ester.

This product is mixed with 30 ml. of 5% methanolic potassium hydroxide and then refluxed, under nitrogen, for two hours. The methanol is removed by vacuum evaporation and 100 ml. of water then added to the residue. The water mixture is extracted with two 30 ml. portions of diethyl ether, and then made slightly acid by the addition of concentrated hydrochloric acid, then again extracted with three 30 ml. portions of fresh diethyl ether. The extracts are combined, then dried over anhydrous sodium sulfate, filtered, and evaporated to dryness yielding (dl)-15$\beta$-hydroxy-9-oxo-prost-13-cis-enoic acid, which is then further purified by recrystallization from ethyl acetate:cyclohexane.

Similarly, by following the same procedure, the following (dl)-15-ether-13-cis prostenoic acid esters are respectively prepared as product rich mixtures and the respective ether and ester groups then stepwise cleaved and the respective (dl)-15-hydroxy-13-cis prostenoic acid esters and (dl)-15-hydroxy-13-cis prostenoic acids isolated:

(dl)-15$\beta$-(2'-methoxyprop-2'-oxy)-9-oxo-prost-13-cis-enoic acid ethyl ester;

(dl)-15$\beta$-(2'-methoxyprop-2'-oxy)-9-oxo-prost-13-cis-enoic acid hexyl ester;

(dl)-6-desbutylene-15$\beta$-(2'-methoxyprop-2'-oxy)-9-oxo-prost-13-cis-enoic acid methyl ester;

(dl)-6-desbutylene-15$\beta$-(2'-methoxyprop-2'-oxy)-9-oxo-prost-13-cis-enoic acid ethyl ester;

(dl)-6-desbutylene-15$\beta$-(2'-methoxyprop-2'-oxy)-9-oxo-prost-13-cis-enoic acid hexyl ester;

(dl)-6-homoethylene-15$\beta$-(2'-methoxyprop-2'-oxy)-9-oxo-prost-13-cis-enoic acid methyl ester;

(dl)-6-homoethylene-15$\beta$-(2'-methoxyprop-2'-oxy)-9-oxo-prost-13-cis-enoic acid ethyl ester; and (dl)-6-homoethylene-15$\beta$-(2'-methoxyprop-2'-oxy)-9-oxo-prost-13-cis-enoic acid hexyl ester.

Similarly, by following the same procedure as above but respectively using (dl)-1-iodo-3-(2'-butoxyprop-2'-oxy)-cis-1-octene and (dl)-1-iodo-3-(1'-pent-1''-oxycyclohexyl-1'-oxy)-cis-1-octene in place of (dl)-1-iodo-3-(2'-methoxyprop-2'-oxy)-cis-1-octene, the following compounds are respectivey prepared as product rich mixtures and the ether and ester groups cleaved and the resulting cleaved products isolated:

(dl)-15$\beta$-(2'-butoxyprop-2'-oxy)-9-oxo-prost-13-cis-enoic acid methyl ester;

(dl)-15$\beta$-(2'-butoxyprop-2'-oxy)-9-oxo-prost-13-cis-enoic acid ethyl ester;

(dl)-15$\beta$-(2'-butoxyprop-2'-oxy)-9-oxo-prost-13-cis-enoic acid hexyl ester;

(dl)-6-desbutylene-15$\beta$-(2'-butoxyprop-2'-oxy)-9-oxo-prost-13-cis-enoic acid methyl ester;

(dl)-6-desbutylene-15$\beta$-(2'-butoxyprop-2'-oxy)-9-oxo-prost-13-cis-enoic acid ethyl ester;

(dl)-6-desbutylene-15$\beta$-(2'-butoxyprop-2'-oxy)-9-oxo-prost-13-cis-enoic acid hexyl ester;

(dl)-6-homoethylene-15$\beta$-(2'-butoxyprop-2'-oxy)-9-oxo-prost-13-cis-enoic acid methyl ester;

(dl)-6-homoethylene-15$\beta$-(2'-butoxyprop-2'-oxy)-9-oxo-prost-13-cis-enoic acid ethyl ester;

(dl)-6-homoethylene-15$\beta$-(2'-butoxyprop-2'-oxy)-9-oxo-prost-13-cis-enoic acid hexyl ester;

(dl)-15$\beta$-(1'-pent-1''-oxycyclohexyl-1'-oxy)-9-oxo-prost-13-cis-enoic acid methyl ester;

(dl)-15$\beta$-(1'-pent-1''-oxycyclohexyl-1'-oxy)-9-oxo-prost-13-cis-enoic acid ethyl ester;

(dl)-15$\beta$-(1'-pent-1''-oxycyclohexyl-1'-oxy)-9-oxo-prost-13-cis-enoic acid hexyl ester;

(dl)-6-desbutylene-15$\beta$-(1'-pent-1''-oxycyclohexyl-1'-oxy)-9-oxo-prost-13-cis-enoic acid methyl ester;

(dl)-6-desbutylene-15$\beta$-(1'-pent-1''-oxycyclohexyl-1'-oxy)-9-oxo-prost-13-cis-enoic acid ethyl ester;

(dl)-6-desbutylene-15$\beta$-(1'-pent-1''-oxycyclohexyl-1'-oxy)-9-oxo-prost-13-cis-enoic acid hexyl ester;

(dl)-6-homoethylene-15$\beta$-(1'-pent-1''-oxycyclohexyl-1'-oxy)-9-oxo-prost-13-cis-enoic acid methyl ester;

(dl)-6-homoethylene-15$\beta$-(1'-pent-1''-oxycyclohexyl-1'-oxy)-9-oxo-prost-13-cis-enoic acid ethyl ester; and (dl)-6-homoethylene-15$\beta$-(1'-pent-1''-oxycyclohexyl-1'-oxy)-9-oxo-prost-13-cis-enoic acid hexyl ester.

EXAMPLE 2

This example illustrates methods, according to the invention, of preparing the reagents and compounds of the invention. In this example 6.7 ml. of a 1.5M n-butyl lithium in hexane solution is admixed to a mixture containing 3.26 g. of (R)-1-iodo-3-(2'-methoxyprop-2'-oxy)-cis-1-octene in 8 ml. of hexane at $-78°$ C under an argon atmosphere. The resulting mixture is stirred and maintained at $-78°$ C, under argon, for 30 minutes. During this time a second mixture containing 2.4 g. of bis-trimethylphosphite copper[(I)] iodide in 60 ml. of diethyl ether is prepared and maintained under argon and cooled to $-78°$ C. At the end of the 30 minute period, previously referred to, the first mixture is admixed to the second mixture and the temperature of the resulting mixture is brought to $-50°$ C. The resulting mixture is periodically monitored by a Gilman test [note; Gilman and Schulze, J. Am. Chem. Soc., v. 47, 2002 (1925], and maintained at $-50°$ C until a negative Gilman test is obtained (about 45 minutes). This reagent mixture is then cooled to $-78°$ C and 1.1 g. of 2-(6-carbomethoxy-hexyl)-1-oxo-cyclopent-2-ene in 3 ml. of diethyl ether is added. The resulting mixture is stirred at $-78°$ C for 2.5 hours yielding a 15$\beta$-(2'-methoxyprop-2'-oxy)-9-oxo-prost-13-cis-enoic acid methyl ester rich mixture. This mixture is poured into 100 ml. of 20% aqueous acetic acid and the resulting mixture stirred at room temperature for 30 minutes yielding a two phase liquid-liquid mixture. The ether layer is separated and extracted with 5% aqueous sodium bicarbonate solution until the ether solution is slightly basic. The ethyl ether is then removed by vacuum evaporation and the resulting residue is stirred at room temperature for 30 minutes with 100 ml. of 15% aqueous ammonia and then extracted with two 50 ml. portions of diethyl ether. The diethyl ether extracts are combined and evaporated under vacuum affording a residue which is then chromatographed over 60 g. of silica gel eluting with gradient mixtures of 15% (vol.) ethyl acetate-85% hexane to 50% (vol.) ethyl acetate-50% hexane, yielding 15β-hydroxy-9-oxo-prost-13-cis-enoic acid methyl ester.

The product is mixed with 30 ml. of 5% methanolic potassium hydroxide and then refluxed, under nitrogen, for 2 hours. The methanol is removed by vacuum evaporation and 100 ml. of water then added to the residue. The water mixture is extracted with two 30 ml. portions of diethyl ether, and then made slightly acid by the addition of concentrated hydrochloric acid, then again extracted with three 30 ml. portions of fresh diethyl ether. The extracts are combined, then dried over anhydrous sodium sulfate, filtered, and evaporated to dryness yielding 15β-hydroxy-9-oxo-prost-13-cis-enoic acid which is then further purified by recrystallization from ethyl acetate-cyclohexane.

Similarly, by following the same procedure as above but in place of 2-(6-carbomethoxy-hexyl)-1-oxo-cyclopent-2-ene respectively using the corresponding products of Preparation 5 as starting materials, the following compounds are respectively prepared as product rich mixtures and the respective ether and ester groups then stepwise cleaved and the respective 15β-hydroxy-13-cis prostenoic acid esters and 15β-hydroxy-13-cis prostenoic acids isolated:

15β-(2'-methoxyprop-2'-oxy)-9-oxo-prost-13-cis-enoic acid ethyl ester;
15β-(2'-methoxyprop-2'-oxy)-9oxo-prost-13-cis-enoic acid hexyl ester;
6-desbutylene-15β-(2'-methoxyprop-2'-oxy)-9-oxo-prost-13-cis-enoic acid methyl ester;
6-desbutylene-15β-(2'-methoxyprop-2'-oxy)-9-oxo-prost-13-cis-enoic acid ethyl ester;
6-desbutylene-15β-(2'-methoxyprop-2'-oxy)-9-oxo-prost-13-cis-enoic acid hexyl ester;
6-homoethylene-15β-(2'-methoxyprop-2'-oxy)-9-oxo-prost-13-cis-enoic acid methyl ester;
6-homoethylene-15β-(2'-methoxyprop-2'-oxy)-9-oxo-prost-13-cis-enoic acid ethyl ester; and
6-homoethylene-15β-(2'-methoxyprop-2'-oxy)-9-oxo-prost-13-cis-enoic acid hexyl ester.

Similarly, by following the same procedure as above but respectively using (R)-1-iodo-3-(2'-butoxyprop-2'-oxy)-cis-1-octene and (R)-1-iodo-3-(1'-pent-1"-oxycyclohexyl-1'-oxy)-cis-1-octene in place of (R)-1-iodo-3-(2'-methoxyprop-2'-oxy)-cis-1-octene, the following compounds are respectively prepared as product rich mixtures and the ether and ester groups stepwise cleaved and the resulting cleaved products isolated:

15β-(2'-butoxyprop-2'-oxy)-9-oxo-prost-13-cis-enoic acid methyl ester;
15β-(2'-butoxyprop-2'-oxy)-9-oxo-prost-13-cis-enoic acid ethyl ester;
15β-(2'-butoxyprop-2'-oxy)-9-oxo-prost-13-cis-enoic acid hexyl ester;
6-desbutylene-15β-(2'-butoxyprop-2'-oxo-prost-13-cis-enoic acid methyl ester;
6-desbutylene-15β-(2'-butoxyprop-2'-oxy-prost-13-cis-enoic acid ethyl ester;
6-desbutylene-15β-(2'-butoxyprop-2'-oxy)-9-oxo-prost-13-cis-enoic acid hexyl ester;
6-homoethylene-15β-(2'-butoxyprop-2'-oxy)-9-oxo-prost-13-cis-enoic acid methyl ester;
6-homoethylene-15β-(2'-butoxyprop-2'-oxy)-9-oxo-prost-13-cis-enoic acid ethyl ester;
6-homoethylene-15β-(2'-butoxyprop-2'-oxy)-9-oxo-prost-13-cis-enoic acid hexyl ester;
15β-(1'-pent-1"-oxycyclohexyl-1'-oxy)-9-oxo-prost-13-cis-enoic acid methyl ester;
15β-(1'-pent-1"-oxycyclohexyl-1'-oxy)-9-oxo-prost-13-cis-enoic acid ethyl ester;
15β-(1'-pent-1"-oxycyclohexyl-1'-oxy)-9-oxo-prost-13-cis-enoic acid hexyl ester;
6-desbutylene-15β-(1'-pent-1"-oxycyclohexyl-1'-oxy)-9-oxo-prost-13-cis-enoic acid methyl ester;
6-desbutylene-15β-(1'-pent-1"-oxycyclohexyl-1'-oxy)-9-oxo-prost-13-cis-enoic acid ethyl ester;
6-desbutylene-15β-(1'-pent-1"-oxycyclohexyl-1'-oxy)-9-oxo-prost-13-cis-enoic acid hexyl ester;
6-homoethylene-15β-(1'-pent-1"-oxycyclohexyl-1'-oxy)-9-oxo-prost-13-cis-enoic acid methyl ester;
6-homoethylene-15β-(1'-pent-1"-oxycyclohexyl-1'-oxy)-9-oxo-prost-13-cis-enoic acid ethyl ester; and
6-homoethylene-15β-(1'-pent-1"-oxycyclohexyl-1'-oxy)-9-oxo-prost-13-cis-enoic acid hexyl ester.

EXAMPLE 3

This example illustrates methods, according to the invention of preparing the reagents and compounds of the invention. In this example 6.7 ml. of a 1.5M n-butyl lithium in hexane solution is admixed to a mixture containing 3.26 g. of (S)-1-iodo-3-(2'methoxyprop-2'-oxy)-cis-1-octene in 8 ml. of hexane at −78° C under an argon atmosphere. The resulting mixture is stirred and maintained at −78° C, under argon, for 30 minutes. During this time a second mixture containing 2.4 g. of bis-trimethylphosphite copper(I) iodide in 60 ml. of diethyl ether is prepared and maintained under argon and cooled to −78° C. At the end of the 30 minute period, previously referred to, the first mixture is admixed to the second mixture and the temperature of the resulting mixture is brought to −50° C. The resulting mixture is periodically monitored by a Gilman test [note; Gilman and Schulze, J. Am. Chem. Soc., v. 47, 2002 (1925)]; and maintained at −50° C until a negative Gilman test is obtained (about 45 minutes). This reagent mixture is then cooled to −78° C and 1.1 g. of 2-(6-carbomethoxy-hexyl)-1-oxo-cyclopent-2-ene in 3 ml. of diethyl ether is added. The resulting mixture is stirred at −78° C for 2.5 hours yielding a retro-15α-(2'-methoxyprop-2'-oxy)-9-oxo-prost-13-cis-enoic acid methyl ester rich mixture. This mixture is poured into 100 ml. of 20% aqueous acetic acid and the resulting mixture stirred at room temperture for 30 minutes yielding a two phase liquid-liquid mixture. The ether layer is separated and extracted with 5% aqueous sodium bicarbonate solution until the ether solution is slightly basic. The ethyl ether is then removed by vacuum evaporation and the resulting residue is stirred at room temperature for 30 minutes with 100 ml. of 15% aqueous ammonia and then extracted with two 50 ml. portions of diethyl ether. The diethyl ether extracts are combined and evaporated under vacuum affording a residue which is then chromatographed over 60 g. of silica gel eluting with gradient mixtures of 15% (vol.) ethyl acetate-85% hexane to 50% (vol.) ethyl acetate-50% hexane, yielding retro-15α-hydroxy-9-oxo-prost-13-cis-enoic acid methyl ester.

This product is mixed with 30 ml. of 5% methanolic potassium hydroxide and then refluxed, under nitrogen, for two hours. The methanol is removed by vacuum evaporation and 100 ml. of water then added to the residue. The water mixture is extracted with two 30 ml. portions of diethyl ether, and then made slightly acid by the addition of concentrated hydrochloric acid, then again extracted with three 30 ml. portions of fresh diethyl ether. The extracts are combined, then dried over anhydrous sodium sulfate, filtered, and evaporated to dryness yielding retro-15α-hydroxy-9-oxo-prost-13-cis-enoic acid which is then further purified by recrystallization from ethyl acetate-cyclohexane.

Similarly, by following the same procedure as above but in place of 2-(6-carbomethoxy-hexyl)-1-oxo-cyclopent-2-ene respectively using the corresponding products of Preparation 5 as starting materials, the following compounds are respectively prepared as product rich mixtures and the respective ether and ester groups then stepwise cleaved and the respective retro-15α-hydroxy-13-cis prostenoic acid esters and retro-15α-hydroxy-13-cis prostenoic acids isolated:

retro-15α-(2'-methoxyprop-2'-oxy)-9-oxo-prost-13-cis-enoic acid ethyl ester;
retro-15α-(2'-methoxyprop-2'-oxy)-9-oxo-prost-13-cis-enoic acid hexyl ester;
retro-6-desbutylene-15α-(2'-methoxyprop-2'-oxy)-9-oxo-prost-13-cis-enoic acid methyl ester;
retro-6-desbutylene-15α-(2'-methoxyprop-2'-oxy)-9-oxo-prost-13-cis-enoic acid ethyl ester;
retro-6-desbutylene-15α-(2'-methoxyprop-2'-oxy)-9-oxo-prost-13-cis-enoic acid hexyl ester;
retro-6-homoethylene-15α-(2'-methoxyprop-2'-oxy)-9-oxo-prost-13-cis-enoic acid methyl ester;
retro-6-homoethylene-15α-(2'-methoxyprop-2'-oxy)-9-oxo-prost-13-cis-enoic acid ethyl ester; and
retro-6-homoethylene-15α-(2'-methoxyprop-2'-oxy)-9-oxo-prost-13-cis-enoic acid hexyl ester.

Similarly, by following the same procedure as above but respectively using (S)-1-iodo-3-(2'-butoxyprop-2'oxy)-cis-1-octene and (S)-1-iodo-3-(1'-pent-1"-oxycyclohexyl-1'-oxy)-cis-1-octene in place of (S)-1-iodo-3-(2'-methoxyprop-2'-oxy)-cis-1octene, the following compounds are respectively prepared as product rich mixtures and the ether and ester groups then stepwise cleaved and the resulting cleaved products isolated:

retro-15α-(2'-butoxyprop-2'-oxy)-9-oxo-prost-13-cis-enoic acid methyl ester;
retro-15α-(2'-butoxyprop-2'-oxy)-9-oxo-prost-13-cis-enoic acid ethyl ester;
retro-15α-(2'butoxyprop-2'-oxy)-9-oxo-prost-13-cis-enoic acid hexyl ester;
retro-6-desbutylene-15α-(2'-butoxyprop-2'-oxy)-9-oxo-prost-13-cis-enoic acid methyl ester;
retro-6-desbutylene-15α-(2'-butoxyprop-2'-oxy)-9-oxo-prost-13-cis-enoic acid ethyl ester;
retro-15α-(2'-butoxyprop-2'-oxy)-6desbutylene-9-oxo-prost-13-cis-enoic acid hexyl ester;
retro-15α-(2'-butoxyprop-2'-oxy)-6-homoethylene-9-oxo-prost-13-cis-enoic acid methyl ester;
retro-15α-(2'-butoxyprop-2'-oxy)-6-homoethylene-9oxo-prost-13-cis-enoic acid ethyl ester;
retro-15α-(2'-butoxyprop-2'-oxy)-6-homoethylene-9-oxo-prost-13-cis-enoic acid hexyl ester;

retro-15α-(1'-pent-1"-oxycyclohexyl-1'-oxy)-9-oxo-prost-13-cis-enoic acid methyl ester;
retro-15α-(1'-pent-1"-oxycyclohexyl-1'-oxy)-9-oxo-prost-13-cis-enoic acid ethyl ester;
retro-15α(1'-pent-1"oxycyclohexyl-1'-oxy)-9-oxo-prost-13-cis-enoic acid hexyl ester;
retro-6-desbutylene-15α-(1'-pent-1"oxycyclohexyl-1'-oxy)-9-oxo-prost-13-cis-enoic acid methyl ester;
retro-6-desbutylene-15α-(1'-pent-1"-oxycyclohexyl-1'-oxy)-9-oxo-prost-13-cis-enoic acid ethyl ester;
retro-6-desbutylene-15α-(1'-pent-1"-oxycyclohexyl-1'-oxy)-9-oxo-prost-13-cis-enoic acid hexyl ester;
retro-6-homoethylene-15α-(1'-pent-1"-oxycyclohexyl-1'-oxy)-9-oxo-prost-13-cis-enoic acid methyl ester;
retro-6-homoethylene-15α-(1'-pent-1"-oxycyclohexyl-1'-oxy)-9-oxo-prost-13-cis-enoic acid ethyl ester; and
retro-6-homoethylene-15α-(1'-pent-1"-oxycyclohexyl)-1'-oxy)-9-oxo-prost-13-cis-enoic acid hexyl ester.

EXAMPLE 4

This example illustrates methods, according to the invention, of preparing the reagents and compounds of the invention. In this example 5 ml. of a 1.5M n-butyl lithium in hexane solution is admixed to a mixture containing 2.5 g. of (dl)-1-iodo-3-(2'-methoxyprop-2'-oxy)-cis-1-octene in 5 ml. of hexane at −78° C under an argon atmosphere. The resulting mixture is stirred and maintained at −78° C, under argon, for 30 minutes. During this time a second mixture containing 1.8 g. of bis-trimethylphosphite copper(I) iodide in 50 ml. of diethyl ether is prepared and maintained under argon and cooled to −78° C. At the end of the 30 minute period, previously referred to, the first solution is admixed to the second solution and the temperature of the resulting mixture is brought to −50° C. The resulting mixture is periodically monitored by a Gilman test [note; Gilman and Schulze, *J. Am. Chem. Soc.*, v. 47, 2002 (1925)], and stirred and maintained at −50° C until a negative Gilman test is obtained (about 20 minutes). This reagent mixture is then cooled to −78° C and 0.298 g. of (dl)-2-(6carbomethoxy-hexyl)-4-(2'-methoxyprop-2'-oxy)-1-oxo-cyclopent-2-ene in 3 ml. of diethyl ether is added. The resulting mixture is stirred at −78° C for two hours yielding a (dl)-11α,15β-bis(2'-methoxyprop-2'-oxy)-9-oxo-prost-13-cis-enoic acid methyl ester rich mixture. This mixture is poured into 100 ml. of 20% aqueous acetic acid and the resulting mixture stirred at room temperature for 30 minutes yielding a two phase liquid-liquid mixture. The ether layer is separated and evaporated under vacuum to remove the ether solvent. The residue is chromatographed on 100 g. of silica gel (which is previously deactivated with 1 g. of formic acid) using a gradient mixture of from one to 1½ to 4:1, by vol., ethyl acetate:hexane mixtures, yielding (dl)-11α,15β-dihydroxy-9-oxo-prost-13-cis-enoic acid methyl ester.

Similarly, by following the same procedure but respectively using (dl)-2-(2-carbomethoxy-ethyl)-4-(2'-methoxyprop-2'-oxy)-1-oxo-cyclopent-2-ene and (dl)-2-(8-carbomethoxy-octyl)-4-(2'-methoxyprop-2'-oxy)-1-oxo-cyclopent-2-ene in place of (dl)-2-(6-carbomethoxy-hexyl)-4-(2'-methoxyprop-2'-oxy)-1-oxo-cyclopent-2-ene, the following enantiomeric mixtures are respectively prepared as product rich mixtures:

(dl)-11α,15β-bis(2'-methoxyprop-2'-oxy)-6-desbutylene-9-oxo-prost-13-cis-enoic acid methyl ester; and (dl)-11α,15β-bis(2'-methoxyprop-2'-oxy)-6-homoethylene-9-oxo-prost-13-cis-enoic acid methyl ester.

Similarly, by following the same procedure using the remaining 11-ether and ester products of Preparation 6 as starting materials, the corresponding enantiomeric mixtures are respectively prepared as product rich mixtures.

Similarly, by following the same procedure using the remaining (dl)-1-iodo-3-ether-cis-1-octene products of Preparation 2 as starting materials, the corresponding (dl)-15-ether analogs of the above products are respectively prepared as product rich mixtures.

The C-11 and C-15 ether groups are then cleaved from each of the above product rich mixtures via treatment with 20% aqueous acetic acid and the respective (dl)-11α,15β-dihydroxy-13-cis prostenoic acid ester products isolated by chromatography, as described above.

EXAMPLE 5

This example illustrtes methods, according to the invention, of preparing the reagents and compounds of the invention. In this example 5 ml. of a 1.5M n-butyl lithium in hexane solution is admixed to a mixture containing 2.5 g. of (R)-1-iodo-3-(2'-methoxyprop-2'-oxy)-cis-1-octene in 5 ml. of hexene at −78° C under an argon atmosphere. The resulting mixture is stirred and maintained at −78° C, under argon, for 30 minutes. During this time a second mixture containing 1.8 g. of bis-trimethylphosphite copper(I) iodide in 50 ml. of diethyl ether is prepared and maintained under argon and cooled to −78° C. At the end of the 30 minute period, previously referred to, the first solution is admixed to the second solution and the temperature of the resulting mixture is brought to −50° C. The resulting mixture is periodically monitored by a Gilman test [note; Gilman and Schulze, *J. Am. Chem. Soc.*, v. 47, 2002 (1925)], and stirred and maintained at −50° C until a negative Gilman test is obtained (about 20 minutes). This reagent mixture is then cooled to −78° C and 0.298 g. of (dl)-2-(6-carbomethoxy-hexyl)-4-(2'-methoxyprop-2'-oxy)-1-oxo-cyclopent-2-ene in 3 ml. of diethyl ether is added. The resulting mixture is stirred at −78° C for 2 hours yielding a 11α,15β-bis(2'-methoxyprop-2'-oxy)-9-oxo-prost-13-cis-enoic acid methyl ester rich mixture. This mixture is poured into 100 ml. of 20% aqueous acetic acid and the resulting mixture stirred at room temperature for 30 minutes yielding a two phase liquid-liquid mixture. The ether layer is separated and evaporated under vacuum to remove the ether solvent. The residue is chromatographed on 100 g. of silica gel (which is previously deactivated with 1 g. of formic acid) using a gradient mixture of from 1 to 1½ to 4:1, by vol., ethyl acetate:hexane mixtures, yielding 11α,15β-dihydroxy-9-oxo-prost-13-cis-enoic acid methyl ester.

Similarly, by following the same procedure but respectively using (dl)-2-(2-carbomethoxy-ethyl)-4-(2'-methoxyprop-2'-oxy)-1-oxo-cyclopent-2-ene and (dl)-2-(8-carbomethoxy-octyl)-4-(2'-methoxyprop-2'-oxy)-1-oxo-cyclopent-2-ene in place of (dl)-2-(6-carbomethoxy-hexyl)-4-(2'-methoxyprop-2'-oxy)-1-oxo-cyclopent-2-ene, the following compounds are respectively prepared as product rich mixtures:

11α, 15β-bis(2'-methoxyprop-2'-oxy)-6-desbutylene-9-oxo-prost-13-cis-enoic acid methyl ester; and 11α, 15β-bis(2'-methoxyprop-2'-oxy)-6-homoethylene-9-oxo-prost-13-cis-enoic acid methyl ester.

Similarly, by following the same procedure using the remaining 11-ether and ester products of Preparation 6 as starting materials, the corresponding compounds are respectively prepared as product rich mixtures.

Similarly, by following the same procedure using the remaining (R)-1-iodo-3-ether-cis-1-octene products of preparation 2 as starting materials, the corresponding 15-ether analogs of the above products are prepared as product rich mixtures.

The C-11 and C-15 ether groups are then cleaved from each of the above product rich mixtures via treatment with 20% aqueous acetic acid and the respective 11α, 15β-dihydroxy-13-cis prostenoic acid ester enantiomers isolated by chromatography, as described above.

EXAMPLE 6

This example illustrates methods, according to the invention, of preparing the reagents and compounds of the invention. In this example 5 ml. of a 1.5M n-butyl lithium in hexane solution is admixed to a mixture containing 2.5 g. of (S)-1-iodo-3-(2'-methoxyprop-2'-oxy)-cis-1-octene in 5 ml. of hexene at −78° C under an argon atmosphere. The resulting mixture is stirred and maintained at −78° C, under argon, for 30 minutes. During this time a second mixture containing 1.8 g. of bistrimethylphosphite copper(I) iodide in 50 ml. of diethyl ether is prepared and maintained under argon and cooled to −78° C. At the end of the 30 minute period, previously referred to, the first solution is admixed to the second solution and the temperature of the resulting mixture is brought to −50° C. The resulting mixture is periodically monitored by a Gilman test [note; Gilman and Schulze, *J. Am. Chem. Soc.*, v 47, 2002 (1965)], and stirred and maintained at −50° C until a negative Gilman test is obtained (about 20 minutes). This reagent mixture is then cooled to −78° C and 0.298 g. of (dl)-2-(6-carbomethoxy-hexyl)-4-(2'-methoxyprop-2'-oxy)-1-oxo-cyclopent-2-ene in 3 ml. of diethyl ether is added. The resulting mixture is stirred at −78° C for 2 hours yielding a retro-11β,15α-bis(2'-methoxyprop-2'-oxy)-9-oxo-prost-13-cis-enoic acid methyl ester rich mixture. This mixture is poured into 100 ml. of 20% aqueous acetic acid and the resulting mixture stirred at room temperature for 30 minutes yielding a two phase liquid-liquid mixture. The ether layer is separated and evaporated under vacuum to remove the ether solvent. The residue is chromatographed on 100 g. of silica gel (which is previously deactivated with 1 g. of formic acid) using a gradient mixture of from 1 to 1½ to 4:1, by vol., ethyl acetate:hexane mixtures, yielding retro-11β, 15α-dihydroxy-9-oxo-prost-13-cis-enoic acid methyl ester.

Similarly, by following the same procedure but respectively using (dl)-2-(2-carbomethoxy-ethyl)-4-(2'-methoxyprop-2'-oxy)-1-oxo-cyclopent-2-ene and (dl)-2-(8-carbomethoxy-octyl)-4-(2'-methoxyprop-2'-oxy)-1-oxo-cyclopent-2-ene in place of (dl)-2-(6-carbomethoxy-hexyl)-4-(2'-methoxyprop-2'-oxy)-1-oxo-cyclopent-2-ene, the following compounds are respectively prepared as product rich mixtures:

retro-11β, 15α-bis(2'-methoxyprop-2'-oxy)-6-desbutylene-9-oxo-prost-13-cis-enoic acid methyl ester; and retro-11β, 15α-bis(2'-methoxyprop-2'-oxy)-6-homo-ethylene-9-oxo-prost-13-cis-enoic acid methyl ester.

Similarly, by following the same procedure using the remaining ester products of Preparation 6, as starting material, the corresponding compounds are respectively prepared as product rich mixtures.

Similarly, by following the same procedure using the remaining (S)-1-iodo-3-ether-cis-1-octene products of Preparation 2 as starting materials, the corresponding 15-ether analogs of the above products are prepared as product rich mixtures.

The C-11 and C-15 ether groups are then cleaved from each of the above product rich mixtures via treatment with 20% aqueous acetic acid and the respective retro-11β, 15α-dihydroxy-13-cis prostenoic acid ester enantiomers isolated by chromatography, as described above.

EXAMPLE 7

This example illustrates methods, according to the invention, of preparing the reagents and compounds of the invention. In this example 5 ml. of a 1M n-butyl lithium in hexane solution is admixed to a mixture containing 2.5 g. of (dl)-1-iodo-3-(2'-methoxyprop-2'-oxy)-cis-1-octene in 5 ml. of hexane at −78° C under an argon atmosphere. The resulting mixture is stirred and maintained at −78° C, under argon, for 30 minutes. During this time a second mixture containing 1.8 g. of bis-trimethylphosphite copper$^{(I)}$ iodide in 50 ml. of diethyl ether is prepared and maintained under argon and cooled to −78° C. At the end of the 30 minute period, previously referred to, the first solution is admixed to the second solution and the temperature of the resulting mixture is brought to −50° C. The resulting mixture is periodically monitored by a Gilman test [note; Gilman and Schulze, J. Am. Chem. Soc., v. 47, 2002 (1925)], and stirred and maintained at −50° C until a negative Gilman test is obtained (about 20 minutes). The reagent mixture is then cooled to −78° C and 0.310 g. of (dl)-2-(6-carbomethoxy-hexyl)-4-(tetrahydropyranyl-2'-oxy)-1-oxo-cyclopent-2-ene in 3 ml. of diethyl ether is added. The resulting mixture is stirred at −78° C for 2 hours yielding a (dl)-15β-(2'-methoxyprop-2'-oxy)-11α-(tetrahydropyranyl-2'-oxy)-prost-13-cis-enoic acid methyl ester rich mixture. This mixture is poured into 100 ml. of 20% aqueous acetic acid and the resulting mixture stirred at room temperature for 30 minutes yielding a two phase liquid-liquid mixture. The ether layer is separated and evaporated under vacuum to remove the ether solvent. The residue is chromatographed on 100 g. of silica gel (which is previously deactivated with 1 g. of formic acid) using a gradient mixture of from 1 to 1½ to 4:1, by vol., of etyl acetate:hexane mixtures, yielding (dl)-15β-hydroxy-9-oxo-11α-(tetrahydropyranyl-2'-oxy)-prost-13-cis-enoic acid methyl ester.

Similarly, by following the same procedure but respectively using (dl)-2-(2-carbomethoxy-ethyl)-4-(tetrahydropyranyl-2'-oxy)-1-oxo-cyclopent-2-ene and (dl)-2-(8-carbomethoxy-octyl)-4-(tetrahydropyranyl-2'-oxy)-1-oxo-cyclopent-2-ene in place of (dl)-2-(6-carbomethoxy-hexyl)-4-(tetrahydropyranyl-2'-oxy)-1-oxo-cyclopent-2-ene, the following enantiomeric mixtures are respectively prepared as product rich mixtures:

(dl)-15β-(2'-methoxyprop-2'-oxy)-6-desbutylene-9-oxo-11α-(tetrahydropyranyl-2'-oxy)-13-cis-enoic acid methyl ester; and (dl)-15β-(2'-methoxyprop-2'-oxy)-6-homoethylene-11α-(tetrahydropyranyl-2'-oxy)-9-oxo-prost-13-cis-enoic acid methyl ester.

Similarly, by following the same procedure using the remaining ester products of Preparation 7, as starting materials, the corresponding enantiomeric mixtures are respectively prepared as product rich mixtures.

Similarly, by following the same procedure using the remaining (dl)-1-iodo-3-ether-cis-1-octene products of Preparation 2 as starting materials, the corresponding 15-ether analogs of the products prepared above as product rich mixtures are also prepared as product rich mixtures.

The C-15 position ether group is then cleaved from each of the above product rich mixtures via treatment with 20% aqueous acetic acid and the respective (dl)-15β-hydroxy-11α-ether-9-oxo-prost-13-cis-enoic acid esters isolated by chromatography, as described above.

EXAMPLE 8

This example illustrates methods, according to the invention, of preparing the reagents and compounds of the invention. In this example 5 ml. of a 1M n-butyl lithium in hexane solution is admixed to a mixture containing 2.5 g. of (R)-1-iodo-3-(2'-methoxyprop-2'-oxy)-cis-1-octene in 5 ml. of hexane at −78° C under an argon atmosphere. The resulting mixture is stirred and maintained at −78° C, under argon, for 30 minutes. During this time a second mixture containing 1.8 g. of bis-trimethylphosphite copper$^{(I)}$ and iodide in 50 ml. of diethyl ether is prepared and maintained under argon and cooled to −78° C. At the end of the 30 minute period, previously referred to, the first solution is admixed to the second solution and the temperature of the resulting mixture is brought to −50° C. The resulting mixture is periodically monitored by a Gilman test [note; Gilman and Schulze, J. Am. Chem. Soc., v. 47, 2002 (1925)], and stirred and maintained at −50° C until a negative Gilman test is obtained (about 20 minutes). This reagent mixture is then cooled to −78° C and 0.310 g. of (dl)-2-(6-carbomethoxy-hexyl)-4-(tetrahydropyranyl-2'-oxy)-1-oxo-cyclopent-2-ene in 3 ml. of diethyl ether is added. The resulting mixture is stirred at −78° C for 2 hours yielding a 15β-(2'-methoxyprop-2'-oxy)-9-oxo-11α-(tetrahydropyranyl-2'-oxy)-prost-13-cis-enoic acid methyl ester rich mixture. This mixture is poured into 100 ml. of 20% aqueous acetic acid and the resulting mixture stirred at room temperature for 30 minutes yielding a two phase liquid-liquid mixture. The ether layer is separated and evaporated under vacuum to remove the ether solvent. The residue is chromatographed on 100 g. of silica gel (which is previously deactivated with 1 g. of formic acid) using a gradient mixture of from 1 to 1½ to 4:1, by vol., of ethyl acetate:hexane mixtures, yielding 15β-hydroxy-9-oxo-11α-(tetrahydropyranyl-2'-oxy)-prost-13-cis-enoic acid methyl ester.

Similarly, by following the same procedure but respectively using (dl)-2-(2-carbomethoxy-ethyl)-4-(tetrahydropyranyl-2'-oxy)-1-oxo-cyclopent-2-ene and (dl)-2-(8-carbomethoxy-octyl)-4-(tetrahydropyranyl-2'-oxy)-1-oxo-cyclopent-2-ene in place of (dl)-2-(6-carbomethoxy-hexyl)-4-(tetrahydropyranyl-2'-oxy)-1-oxo-cyclopent-2-ene, the following compounds are respectively prepared as product rich mixtures:

15β-(2'-methoxyprop-2'-oxy)-6-desbutylene-9-oxo-11α-(tetrahydropyranyl-2'-oxy)-13-cis-enoic acid methyl ester; and 15β-(2'-methoxyprop-2'-oxy)-6-homoethylene-11α-(tetrahydropyranyl-2'-oxy)-9-oxo-prost-13-cis-enoic acid methyl ester.

Similarly, by following the same procedure using the remaining ester products of Preparation 7, as starting materials, the corresponding 11α, 15β-diethers are respectively prepared as product rich mixtures.

Similarly, by following the same procedure using the remaining (R)-1-iodo-3-ether-cis-1-octene products of Preparation 2 as starting materials, the corresponding 15-ether analogs of the products prepared above as product rich mixtures, are also prepared as product rich mixtures and isolated as above.

The C-15 position ether group is then cleaved from each of the above product rich mixtures via treatment with 20% aqueous acetic acid and the respective 15β-hydroxy-11α-ether 9-oxo-prost-13-cis-enoic acid esters isolated by chromatography, as described above.

EXAMPLE 9

This example illustrates methods, according to the invention, of preparing the reagents and compounds of the invention. In this example 5 ml. of a 1M n-butyl lithium in hexane solution is admixed to a mixture containing 2.5 g. of (S)-1-iodo-3-(2'-methoxyprop-2'-oxy)-cis-1-octene in 5 ml. of hexane at −78° C under an argon atmosphere. The resulting mixture is stirred and maintained at −78° C, under argon, for 30 minutes. During this time a second mixture containing 1.8 g. of bistrimethylphosphite copper$^{(I)}$ iodide in 50 ml. of diethyl ether is prepared and maintained under argon and cooled to −78° C. At the end of the 30 minute period, previously referred to, the first solution is admixed to the second solution and the temperature of the resulting mixture is brought to −50° C. The resulting mixture is periodically monitored by a Gilman test [note; Gilman and Schulze, *J. Am. Chem. Soc.*, v. 47, 2002 (1925)], and stirred and maintained at −50° C until a negative Gilman test is obtained (about 20 minutes). This reagent mixture is then cooled to −78° C and 0.310 g. of (dl)-2-(6-carbomethoxy-hexyl)-4-(tetrahydropyranyl-2'-oxy)-1-oxo-cyclopent-2-ene in 3 ml. of diethyl ether is added. The resulting mixture is stirred at −78° C for 2 hours yielding a retro-15α-(2'-methoxyprop-2'-oxy)-9-oxo-11β-(tetrahydropyranyl-2'-oxy)-prost-13-cis-enoic acid methyl ester rich mixture. This mixture is poured into 100 ml. of 20% aqueous acetic acid and the resulting mixture stirred at room temperature for 30 minutes yielding a two phase liquid-liquid mixture. The ether layer is separated and evaporated under vacuum to remove the ether solvent. The residue is chromatographed on 100 g. of silica gel (which is previously deactivated with 1 g. of formic acid) using a gradient mixture of from 1 to 1½ to 4:1, by vol, of ethyl acetate:-hexane mixtures, yielding retro-15α-hydroxy-9-oxo-11β-(tetrahydropyranyl-2'-oxy)- prost-13-cis-enoic acid methyl ester.

Similarly, by following the same procedure but respectively using (dl)-2-(2-carbomethoxy-ethyl)-4-(tetrahydropyranyl-2'-oxy)-1-oxo-cyclopent-2-ene and (dl)-2-(8-carbomethoxyoctyl)-4-(tetrahydropyranyl-2'-oxy)-1-cyclopent-2-ene in place of (dl)-2-(6-carbomethoxy-hexyl)-4-(tetrahydropyranyl-2'-oxy)-1-oxo-cyclopent-2-ene, the following compounds are respectively prepared as product rich mixtures:

retro-15α-(2'-methoxyprop-2'-oxy)-6-desbutylene-11β-(tetrahydropyranyl-2'-oxy)-9-oxo-prost-13-cis-enoic acid methyl ester and retro-15α-(2'-methoxyprop-2'-oxy)-6-homoethylene-11β-(tetrahydropyranyl-2'-oxy)-9-oxo-prost-13-cis-enoic acid methyl ester.

Similarly, by following the same procedure using the remaining ester products of Preparation 7 as starting materials, the corresponding retro-11β,15α-diethers are respectively prepared as product rich mixtures.

Similarly, by following the same procedure using the remaining (S)-1-iodo-3-ether-cis-1-octene products of Preparation 2 as starting materials, the corresponding 15-ether analogs of the products prepared above as product rich mixtures, are also prepared as product rich mixtures and isolated as above.

The C-15 position ether group is then cleaved from each of the above product rich mixtures via treatment with 20% aqueous acetic acid and the retro-15α-hydroxy-11β-ether-9-oxo-prost-13-cis-enoic acid esters isolated by chromatography, as described above.

EXAMPLE 10

This example illustrates microbiological methods for cleaving ester groups from 13-cis prostenoic acid esters. In this example 129 mg. of (dl)-11α,15β-dihydroxy-9-oxo-prost-13-cis-enoic acid methyl ester is admixed with 60 ml. of a pancreatic lipase preparation, prepared according to Preparation 8, at room temperature. The mixture is emulsified by sonication for 2 minutes and then stirred at room temperature for 10 minutes while controlling the pH of the mixture at pH 7 by the controlled addition of 0.1M aqueous sodium hydroxide solution. The mixture is then poured into 400 ml. of acetone, filtered and evaporated, under vacuum, and the resulting residue is extracted with four 20 ml. portions of ethyl acetate. The extracts are combined and concentrated by vacuum evaporation. The concentrate is chromatographed, on silica gel, eluting with a 75:25:2 (volume proportion) mixture of benzene, tetrahydrofuran and formic acid. The prostanoic acid product is recovered with the tetrahydrofuran fraction and then recrystallized with ethyl acetate-cyclohexane affording (dl)-11α15β-dihydroxy-9-oxo-prost-13-cis-enoic acid.

Similarly, by following the same procedure, the 11,15-dihydroxy and 15-hydroxy-11-ether-9-oxo-13-cis prostenoic acid ester products prepared and isolated in Examples 4, 5, 6, 7, 8 and 9 are respectively cleaved to the corresponding acids.

EXAMPLE 11

This exammple illustrates the epimerization at the 15-position of 13-cis prostaglandin derivatives. In this example 0.081 g. of triethylamine is added to 0.352 g. of (dl)-15β-hydroxy-9-oxo-prost-13-cis-enoic acid methyl ester in 20 ml. of methylene chloride at −20° C. A solution containing 0.114 g. of methanesulfonyl chloride in 5 ml. of methylene chloride is then added dropwise, over a period of thirty minutes, and the resulting mixture is warmed to room temperature and poured into 30 ml. of water forming a two phase liquid-liquid mixture. The methylene chloride layer is separated and evaporated to dryness, under vacuum. The resulting residue is stirred in 30 ml of 80% aqueous acetone for 16 hours at room temperature, and then evaporated to dryness under vacuum. Twenty milliliters of water is added to the resulting residue and the resulting mixture extracted with three 20 ml. portions of ethyl ether. The ethyl ether extracts are combined, evaporated under vacuum affording a residue which is then treated with 30 ml. of 5% methanolic potassium hydroxide and refluxed, under nitrogen, for 2 hours and then evaporated to dryness. 100 Ml. of water is added to the residue and the resulting mixture extracted with two 30 ml. portions of diethyl ether. The aqueous layer is acidified with concentrated hydrochloric acid to a pH of about 4 and then extracted with three 30 ml. portions of ethyl ether. The combined diethyl ether extracts are combined, dried over anhydrous sodium sulfate, filtered, and evaporated to dryness affording as a residue a mixture of:

(dl)-15α-hydroxy-9-oxo-prost-13-cis-enoic acid and
(dl)-15β-hydroxy-9-oxo-prost-13-cis-enoic acid.

The respective diastereoisomers are then separated by preparative thin-layer chromatography using a solvent mixture of benzene:tetrahydrofuran:formic acid in a volume ratio of 75:75:2.

Similarly, by following the same procedure as above, the 15β-hydroxy-13-cis-prostanoic acid esters, prepared in Examples 1, 2 and 3, are respectively epimerized into mixtures of the corresponding 15α- and 15β- isomers, which are then cleaved and separated into their respective isomers by thin-layer chromatography (or in the case where the products of Example 1 are used as starting materials, into two (dl) pairs — I.e. (dl)--α-and (dl)-15β, as described above.

EXAMPLE 12

This example illustrates methods of epimerizing 13-cis prostaglandin derivatives having an ether function at the C-11 position. In this example 0.081 g. of triethylamine is added to 0.452 g. of (dl)-15β-hydroxy-9-oxo-11α-(tetrahydropyranyl-2'-oxy)-prost-13-cis-enoic acid methyl ester in 20 ml. of methylene chloride at −20° C. A solution containing 0.114 g. of methanesulfonyl chloride in 5 ml. of methylene chloride is then added dropwise, over a period of thirty minutes, and the resulting mixture warmed to room temperature and poured into 30 ml. of water forming a two phase liquid-liquid system. The methylene chloride layer is removed and evaporated to dryness affording a residue which is then stirred in 30 ml. of 80% aqueous acetone for 16 hours. The mixture is then evaporated and 20 ml. of water added to the resulting residue, followed by extraction with three 20 ml. portions of ethyl ether. The ethyl ether extracts are then combined and evaporated to dryness, under vacuum, yielding a residue which is then added to 20 ml. of 65% aqueous acetic acid and stirred at room temperature for 16 hours. This mixture is then evaporated, under vacuum, and the resulting residue treated with pacreatic lipase, according to the procedure described in Example 10, yielding a mixture of:

(dl)-11α,15α-dihydroxy-9-oxo-prost-13-cis-enoic acid and
(dl)-11α,15β-dihydroxy-9-oxo-prost-13-cis-enoic acid.

The respective isomers are then separated by preparative thin-layer chromatography as described in Example 11.

Similarly, by following the same procedure as above, the 15β-hydroxy-13-cis prostenoic acid ester 11-ethers, prepared in Examples 7, 8 and 9, are epimerized to mixtures of the corresponding 15α- and 15β- isomers which are acid cleaved and enzymatically hydrolyzed as described above, and then separated into their respective (dl)-15α- and (dl)-15β-hydroxy-11α-hydroxy-prost-13-cis-enoic acids where the products of Example 7 are used as starting materials. Where the products of Examples 8 and 9 are used as starting materials, the resulting product is a mixture of the corresponding 15α and 15β-or retro-15α- and 15β-diastereomers, which are then separated (isolated) into the respective isomers by thin-layer chromatography as described in Example 11.

EXAMPLE 13

This example illustrates methods of reducing 9-oxo groups to 9-hydroxy groups. In this example 12.1 g. of pure 11α,15β-dihydroxy-9-oxo-prost-13-cis-enoic acid methyl ester is dissolved in 150 ml. of methanol and then cooled to about 0° C in an ice bath. Fifty milliliters of methanol containing 2 g. of sodium borohydride solution is added dropwise until all of the methyl ester starting material is consumed as determined by thin-layer chromatographic analysis. The reaction mixture is then poured into water and extracted five times with methylene chloride. The combined methylene chloride extracts are washed sequentially with water, then saturated aqueous sodium chloride and dried over anhydrous sodium sulfate. The solvent is removed by evaporation affording a mixture of 9α,11α,15β-trihydroxy-prost-13-cis-enoic acid methyl ester and 9β,11α,15β-trihydroxy-prost-13-cis-enoic acid methyl ester, which is then separated into the respective 9α-hydroxy and 9β-hydroxy isomers by column chromatography over silica gel eluting with ethyl acetate-hexane.

The methyl ester group is then cleaved from each isomer enzymatically, according to the procedure described in Example 10, affording, respectively, 9α,-11α,15β-trihydroxy-prost-13-cis-enoic acid and 9β,11α,15β-trihydroxy-prost-13-cis-enoic acid.

Similarly, by following the same procedure as above, the 9-oxo-prost-13-cis-enoic acid ester products of Examples 1–9 are reduced to the corresponding 9α-hydroxy- and 9β-hydroxy-prost-13-cis-enoic acid ester derivatives and then separated into their respective isomers (or (dl) pairs) by column chromatography, as described above, and enzymatically converted to the corresponding acids according to the procedure described in Example 10.

Obviously many modifications of the invention, described herein above and below and in the claims, can be made without departing from the essence and scope thereof.

What is claimed is:

1. A 13-cis prostaglandin compound selected from the group of isomers having the formulas:

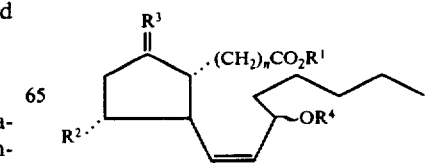

-continued

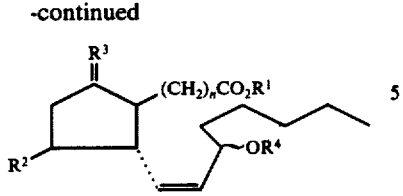

wherein n is a whole integer of from two through eight; R¹ is hydrogen, alkyl having from one through ten carbon atoms, chloroethyl, dichloroethyl, or trichloroethyl; R² is hydrogen; R³ is oxo; and ∼OR⁴ is hydroxy or acid labile ether having from three through ten carbon atoms wherein the wavy bond line indicates either the α or β configuration or isomer mixtures of the α and β configurations;
and mixtures of such isomers and pharmaceutically acceptable salts of such isomers and isomer mixtures wherein R¹ is hydrogen.

2. The compound of claim 1 wherein said compound is an isomer or racemic mixture selected from the group having the formulas:

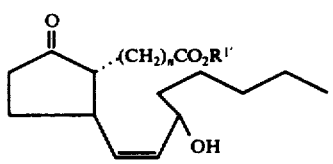

(III)

(IIIr)

-continued

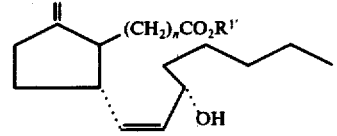

wherein R¹' is hydrogen or methyl; and pharmaceutically acceptable salts thereof.

3. The compound of claim 1 wherein said compound is an isomer or racemic mixture selected from the group having the formulas:

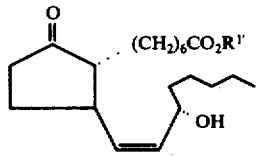

(IV)

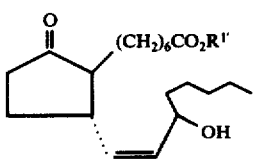

(IVr)

wherein R¹' is hydrogen or methyl; and pharmaceutically acceptable salts thereof.

4. The compound of claim 1 wherein n is 6 and R¹ is hydrogen or methyl, and said pharmaceutically acceptable salts thereof.

5. The compound of claim 1 wherein n is 6 and said pharmaceutically acceptable salts thereof.

6. The compound of claim 5 wherein OR⁴ is hydroxy, and said pharmaceutically acceptable salts thereof.

7. The compound of claim 1 wherein R² is hydrogen and OR⁴ is hydroxy, and said pharmaceutically acceptable salts thereof.

* * * * *